US009182504B2

United States Patent
Nishino et al.

(10) Patent No.: US 9,182,504 B2
(45) Date of Patent: Nov. 10, 2015

(54) RADIATION DETECTOR AND RADIOLOGICAL IMAGE RADIOGRAPHING APPARATUS

(75) Inventors: Naoyuki Nishino, Kanagawa (JP);
Naoto Iwakiri, Kanagawa (JP);
Haruyasu Nakatsugawa, Kanagawa (JP); Keiichiro Sato, Kanagawa (JP);
Yasunori Ohta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 45 days.

(21) Appl. No.: 13/588,557

(22) Filed: Aug. 17, 2012

(65) Prior Publication Data
US 2013/0048866 A1 Feb. 28, 2013

(30) Foreign Application Priority Data

Aug. 26, 2011 (JP) ............... P2011-185063
Jul. 27, 2012 (JP) ............... P2012-167563

(51) Int. Cl.
*G01T 1/20* (2006.01)
*G01T 1/202* (2006.01)
*A61B 6/00* (2006.01)

(52) U.S. Cl.
CPC ............. *G01T 1/202* (2013.01); *A61B 6/4216* (2013.01); *A61B 6/4283* (2013.01)

(58) Field of Classification Search
CPC ......... G01T 1/202; G01T 1/20; G01T 1/2018; G01T 1/2023; G01T 1/2006; G01T 1/2008
USPC ........................ 250/484.4, 370.11
See application file for complete search history.

(56) References Cited

U.S. PATENT DOCUMENTS 4,769,549 A * 9/1988 Tsuchino et al. .......... 250/484.4
4,855,598 A * 8/1989 Ohgoda et al. ................ 250/582
(Continued)

FOREIGN PATENT DOCUMENTS

JP S60-200189 A 10/1985
JP H03-211500 A 9/1991
(Continued)

OTHER PUBLICATIONS

An Office Action; "Notice of Reasons for Rejection," issued by the Japanese Patent Office on Aug. 19, 2014, which corresponds to Japanese Patent Application No. 2012-167563 and is related to U.S. Appl. No. 13/588,557; with English language translation.
(Continued)

*Primary Examiner* — David Porta
*Assistant Examiner* — Djura Malevic
(74) *Attorney, Agent, or Firm* — Studebaker & Brackett PC

(57) ABSTRACT

A radiation detector and a radiological image radiographing apparatus capable of improving the quality of an obtained radiological image without causing an additional cost are provided. A first scintillator configured to include columnar crystals generating first light corresponding to a radiation emitted through a TFT substrate is laminated on the other surface of the TFT substrate that has a first photoelectric conversion element, which has one surface from which a radiation is emitted and the other surface from which at least one of the first light and the second light is emitted and which generates electric charges corresponding to the light, and a first switching element. A second scintillator which generates second light corresponding to a radiation emitted through the first scintillator and has different energy characteristics of absorbed radiations from the first scintillator is laminated on a surface of the first scintillator not facing the TFT substrate.

28 Claims, 29 Drawing Sheets

(56) References Cited

U.S. PATENT DOCUMENTS

| | | | | |
|---|---|---|---|---|
| 4,870,667 | A * | 9/1989 | Brunnett et al. | 378/19 |
| 4,985,633 | A * | 1/1991 | Vieux et al. | 250/486.1 |
| 5,029,247 | A * | 7/1991 | Anno et al. | 250/214 VT |
| 5,047,624 | A * | 9/1991 | Anno et al. | 250/214 VT |
| 5,138,167 | A * | 8/1992 | Barnes | 250/370.01 |
| 5,149,971 | A * | 9/1992 | McElhaney et al. | 250/361 R |
| 5,179,284 | A * | 1/1993 | Kingsley et al. | 250/370.11 |
| 5,449,449 | A * | 9/1995 | Vieux et al. | 205/201 |
| 5,548,123 | A * | 8/1996 | Perez-Mendez et al. | 250/370.11 |
| 5,825,032 | A * | 10/1998 | Nonaka et al. | 250/370.09 |
| 5,981,959 | A * | 11/1999 | Apte | 250/483.1 |
| 6,895,077 | B2 * | 5/2005 | Karellas et al. | 378/98.3 |
| 7,263,165 | B2 * | 8/2007 | Ghelmansarai | 378/98.8 |
| 7,315,027 | B2 * | 1/2008 | Okada et al. | 250/370.11 |
| 7,514,698 | B2 * | 4/2009 | Isoda | 250/484.4 |
| 7,522,695 | B2 * | 4/2009 | Nishide et al. | 378/4 |
| 7,531,817 | B2 * | 5/2009 | Nagata et al. | 250/483.1 |
| 7,834,321 | B2 * | 11/2010 | Yorkston et al. | 250/370.09 |
| 7,893,405 | B2 * | 2/2011 | Nagano et al. | 250/370.11 |
| 8,569,707 | B2 * | 10/2013 | Watanabe et al. | 250/369 |
| 2001/0054694 | A1 * | 12/2001 | Kusuyama et al. | 250/367 |
| 2002/0027201 | A1 * | 3/2002 | Agano | 250/370.11 |
| 2003/0047697 | A1 * | 3/2003 | Iwabuchi et al. | 250/584 |
| 2003/0169847 | A1 * | 9/2003 | Karellas et al. | 378/98.3 |
| 2005/0051736 | A1 * | 3/2005 | Isoda et al. | 250/484.4 |
| 2005/0067586 | A1 * | 3/2005 | Yanagita et al. | 250/484.4 |
| 2005/0077479 | A1 * | 4/2005 | Isoda et al. | 250/484.4 |
| 2005/0285044 | A1 * | 12/2005 | Mollov | 250/370.11 |
| 2006/0151708 | A1 * | 7/2006 | Bani-Hashemi et al. | 250/370.11 |
| 2007/0040125 | A1 * | 2/2007 | Sato et al. | 250/367 |
| 2007/0051896 | A1 * | 3/2007 | Okada et al. | 250/370.11 |
| 2007/0205380 | A1 * | 9/2007 | Isoda | 250/484.4 |
| 2008/0011960 | A1 * | 1/2008 | Yorkston et al. | 250/370.09 |
| 2010/0193691 | A1 | 8/2010 | Ishii et al. | |
| 2011/0006213 | A1 * | 1/2011 | Sato et al. | 250/367 |
| 2011/0180890 | A1 * | 7/2011 | Sato | 257/429 |
| 2011/0233411 | A1 * | 9/2011 | Nishino et al. | 250/361 R |
| 2011/0303849 | A1 * | 12/2011 | Tredwell et al. | 250/362 |
| 2012/0298876 | A1 * | 11/2012 | Kaneko et al. | 250/366 |
| 2013/0026377 | A1 * | 1/2013 | Ichimura et al. | 250/367 |
| 2013/0048864 | A1 * | 2/2013 | Nakatsugawa | 250/366 |
| 2013/0284934 | A1 * | 10/2013 | Kaneko et al. | 250/361 R |

FOREIGN PATENT DOCUMENTS

| | | |
|---|---|---|
| JP | H07-27865 A | 1/1995 |
| JP | H07-084053 A | 3/1995 |
| JP | 2001-074845 A | 3/2001 |
| JP | 2002-181941 A | 6/2002 |
| JP | 2009-133837 A | 6/2009 |
| JP | 2010-025620 A | 2/2010 |
| JP | 2010-121997 A | 6/2010 |
| JP | 2011-000235 A | 1/2011 |
| JP | 2011-017683 A | 1/2011 |
| JP | 2011-022132 A | 2/2011 |
| JP | 2011-128165 A | 6/2011 |

OTHER PUBLICATIONS

"Notice of First Office Action," issued by the State Intellectual Property Office of the Peoples Republic of China on Apr. 3, 2015, which corresponds to Chinese Patent Application No. 201210298996.X and is related to U.S. Appl. No. 13/588,557; with English language translation.

* cited by examiner

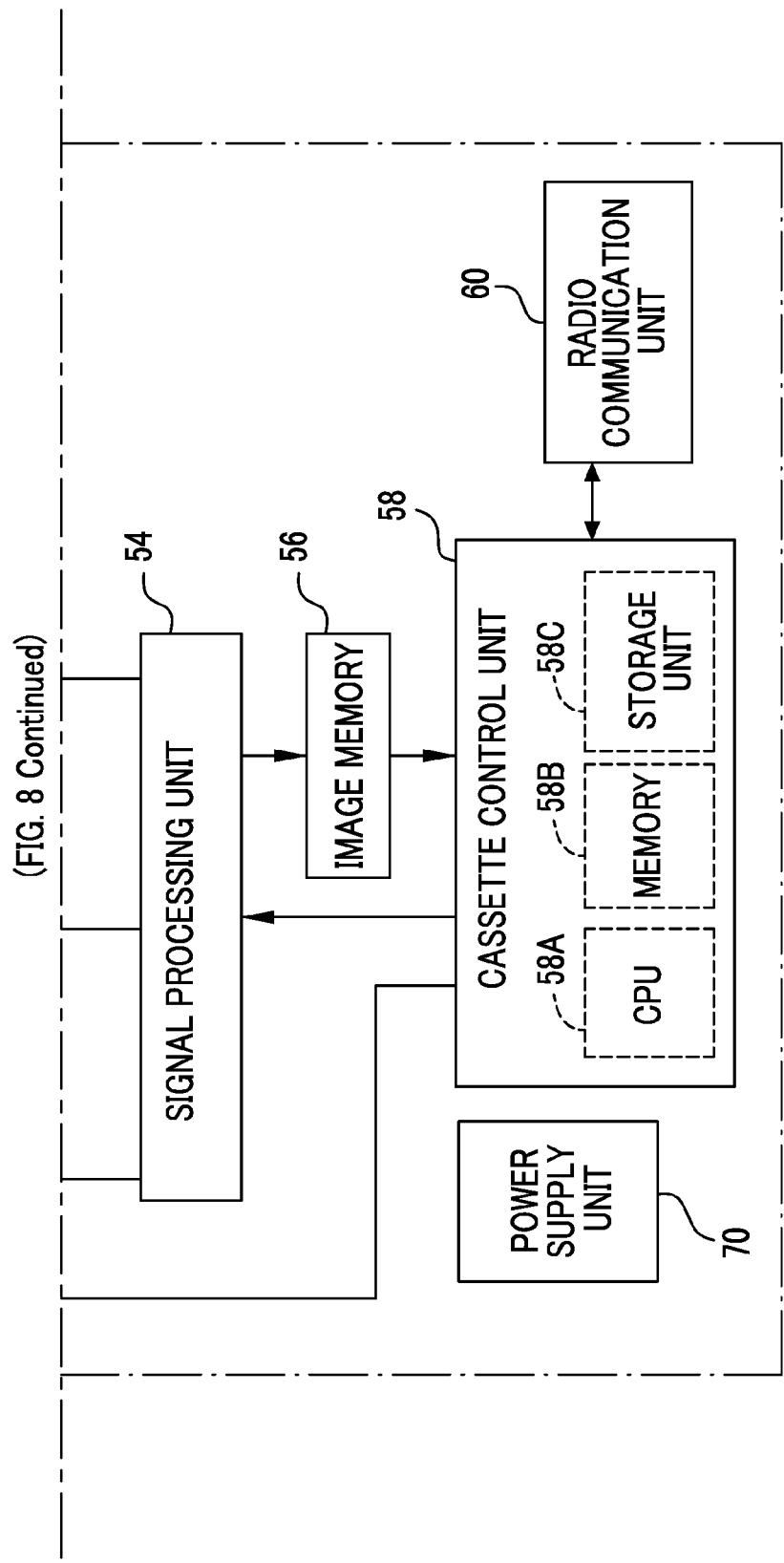

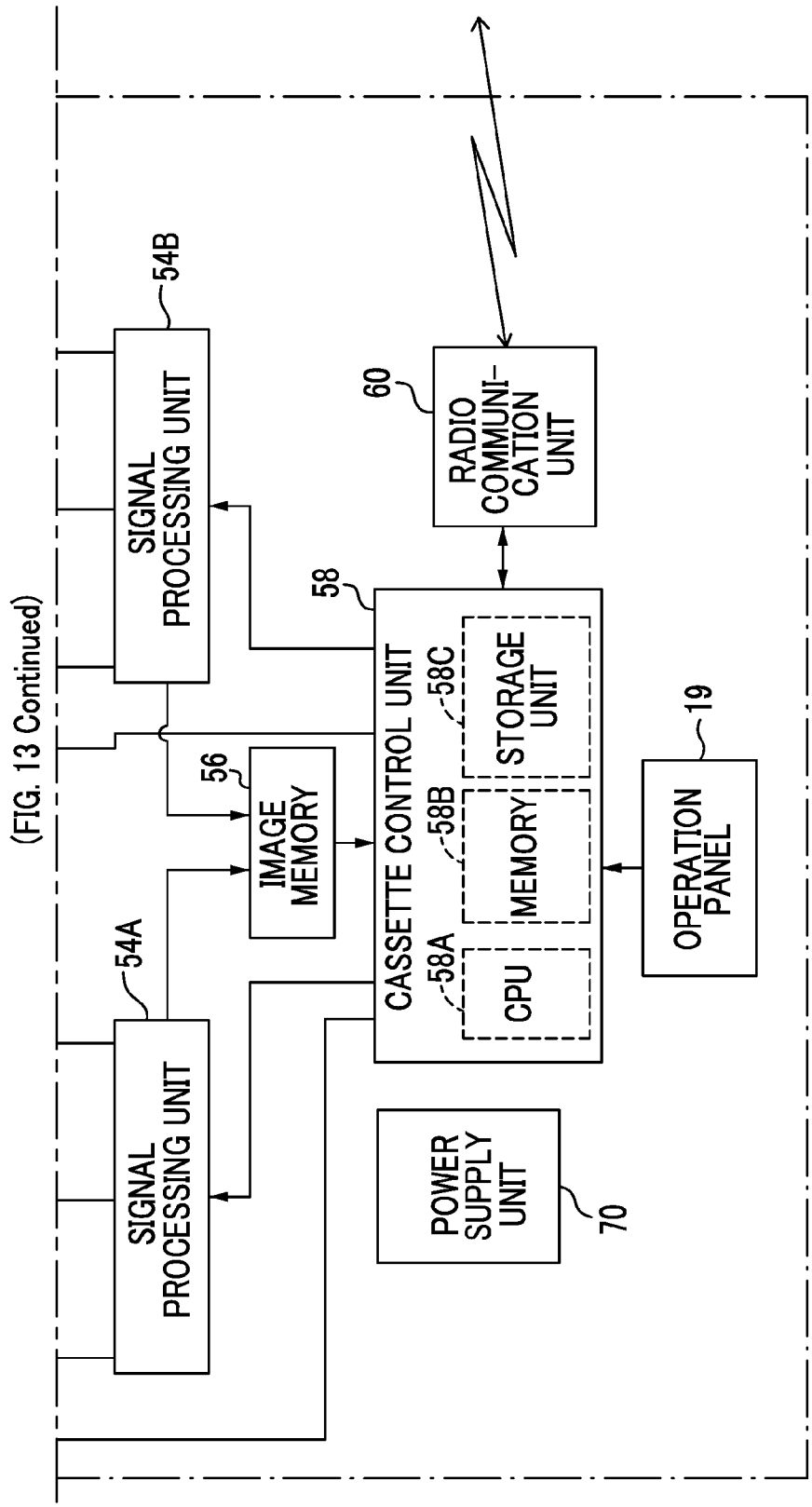

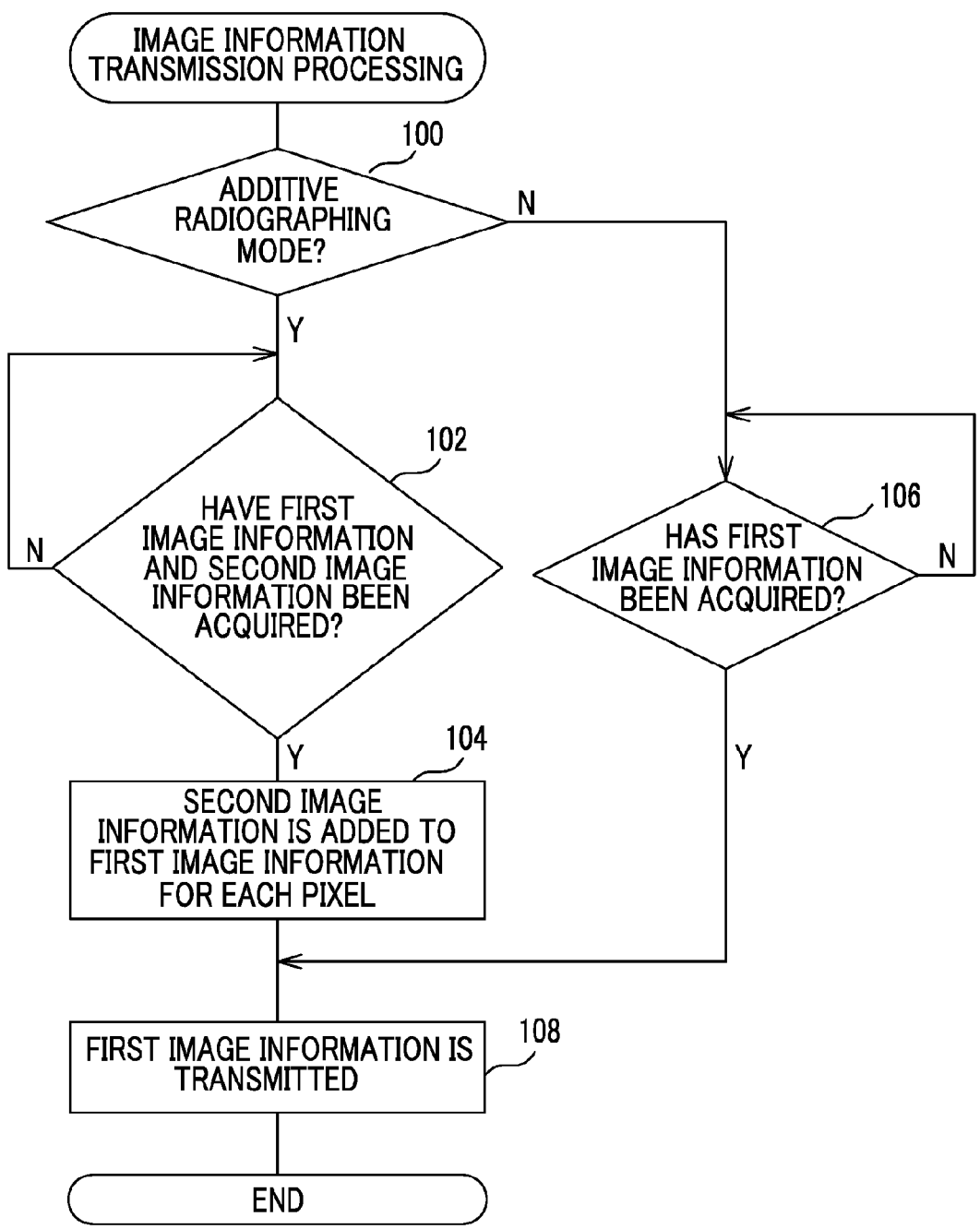

RADIATION DETECTOR AND RADIOLOGICAL IMAGE RADIOGRAPHING APPARATUS

BACKGROUND OF THE INVENTION

1. Field of the Invention

The present invention relates to a radiation detector and a radiological image radiographing apparatus. In particular, the present invention relates to a radiation detector which detects an emitted radiation and a radiological image radiographing apparatus which radiographs a radiological image expressed by the radiation detected by the radiation detector.

2. Description of the Related Art

In recent years, a radiation detector such as an FPD (Flat Panel Detector), which has a radiation-sensitive layer disposed on a TFT (Thin Film Transistor) active matrix substrate which can convert a radiation such as an X-ray directly into digital data, has been put to practical use. A radiological image radiographing apparatus using this radiation detector is advantageous in that an image can be immediately checked and accordingly fluoroscopy (moving image radiographing), which is for radiographing a radiological image continuously, can be performed compared with a radiological image radiographing apparatus using an X-ray film or an imaging plate in the related art.

As such a radiation detector, various types of radiation detectors have been proposed. For example, there is an indirect conversion type radiation detector in which a radiation is first converted into light by a scintillator, such as CsI:Tl or GOS ($Gd_2O_2S$:Tb), and the converted light is converted into electric charges and stored in a sensor section, such as a photodiode. In the radiological image radiographing apparatus, the electric charges stored in the radiation detector are read as an electric signal, and the read electric signal is amplified by an amplifier and is then converted into digital data by an A/D (analog to digital) converter.

Meanwhile, there has been a radiation detector with a phosphor layer (scintillator), which includes columnar crystals with relatively high sensitivity, in order to reduce the amount of exposure to a subject (patient).

In this technique, in order to increase the amount of radiation absorbed by the columnar crystals, it is necessary to make a scintillator layer considerably thick, as is also apparent from FIG. 11 in JP2008-51793A as an example. However, an increase in the thickness of the scintillator layer leads to an increase in cost. In addition, as the thickness increases, it is necessary to increase the porosity in an initial portion (base portion) of the columnar crystals. As a result, there has been a problem in that the amount of emitted light in the initial portion is reduced.

That is, the diameter of a columnar portion changes with a predetermined fluctuation during the vapor deposition of the columnar crystals. Therefore, as the thickness increases, a probability that the maximum value of the fluctuation will occur is increased. As a result, a possibility that columnar portions will contact each other is increased. In addition, once columnar portions contact each other, a possibility that the columnar portions will be fused is increased. This leads to blurring of an image. In addition, there is also a predetermined fluctuation in the length of the columnar portion. Accordingly, if there is adhesion of foreign matter on the substrate on which the columnar portions are vapor-deposited, the length of an abnormally grown columnar portion also increases as the thickness increases. For this reason, a process of reducing the length of an abnormally grown columnar portion by pressure or the like is required after the vapor deposition process. This makes the manufacturing process complicated. In addition, a normal columnar portion around the abnormally grown columnar portion may be damaged due to the pressure. For this reason, when the scintillator layer is made thick in order to prevent the above-described fusion, it is necessary to set the filling rate of columnar crystals low (set the porosity of the initial portion high) in advance in order to prevent the above-described fusion and to prevent the complication of the process due to abnormal growth of columnar portions and damage to normally grown columnar portions. For example, WO2010/007807A discloses a scintillator in which the filling rate of columnar crystals is set to 75% to 90% when the thickness of the scintillator layer of the columnar crystals is 100 μm to 500 μm or more. In addition, JP2006-58099A discloses a scintillator in which the filling rate of columnar crystals is set to 70% to 85% when the thickness of the scintillator layer of the columnar crystals is 500 μm or more.

As a technique which can be applied to solve the above-described problems, JP2002-181941A discloses a radiological digital image radiographing apparatus that is excellent in sharpness and has high detection efficiency. Specifically, JP2002-181941A discloses a radiological digital image radiographing apparatus which has a phosphor layer formed of phosphor particles and binder resin and is characterized in that the phosphor layer is configured to include a first phosphor layer with a plate shape and a second phosphor layer which is provided in contact with the first phosphor layer and provided corresponding to each pixel and which has an approximately columnar shape.

In addition, JP2002-181941A discloses a configuration in which the approximately columnar second phosphor layer, the plate-shaped first phosphor layer, and a substrate where a photoelectric conversion element is provided are laminated sequentially from the emission side of radiation.

Moreover, in order to provide a radiological image detector capable of improving the light conversion efficiency and acquiring a high-quality image, JP2010-121997A discloses a radiological image detector in which a wavelength conversion layer including a phosphor, which receives a radiation and converts the radiation into light with a longer wavelength than the radiation, and a detector, which detects the light converted by the wavelength conversion layer and converts the light into an image signal showing a radiological image, are laminated and which is characterized in that the wavelength conversion layer is formed by laminating at least two layers of a first phosphor layer and a second phosphor layer, the second phosphor layer and the first phosphor layer are disposed in this order from the detector side, and the first phosphor layer includes absorbent to absorb the light converted by the first phosphor layer.

In addition, JP2010-121997A discloses a configuration in which a substrate where a photoelectric conversion element is provided, a plate-shaped second phosphor layer formed of GOS, and a columnar first phosphor layer formed of CsI are laminated sequentially from the emission side of radiation.

SUMMARY OF THE INVENTION

In the technique disclosed in JP2002-181941A, however, the second phosphor layer which has relatively high sensitivity and an approximately columnar shape is disposed at the radiation incidence side, but light emitted from the second phosphor layer is received through the first phosphor layer. Accordingly, there has been a problem in that the high quality is not necessarily obtained.

In addition, also in the technique disclosed in JP2010-121997A, light from the first phosphor layer which has relatively high sensitivity and a columnar shape is received by the substrate through the plate-shaped second phosphor layer. Accordingly, similar to the technique disclosed in JP2002-181941A, there has been a problem in that the high quality is not necessarily obtained.

The present invention has been made in view of the above-mentioned problems and an object of the present invention is to provide a radiation detector and a radiological image radiographing apparatus capable of improving the quality of an obtained radiological image without causing an increase in cost.

In order to achieve the above-described object, according to a first aspect of the present invention, there is provided a radiation detector including: a substrate having a first photoelectric conversion element, which has one surface from which a radiation is emitted and the other surface from which light is emitted and which generates electric charges corresponding to the light, and a first switching element for reading the electric charges generated by the first photoelectric conversion element; a first phosphor layer which is laminated on the other surface of the substrate, generates first light corresponding to a radiation emitted through the substrate, and is configured to include columnar crystals; and a second phosphor layer which is laminated on a surface of the first phosphor layer not facing the substrate, generates second light corresponding to a radiation emitted through the first phosphor layer, and has different energy characteristics of absorbed radiations from the first phosphor layer. Light emitted from the other surface is at least one of the first light and the second light.

In the radiation detector according to the first aspect of the present invention, the first phosphor layer which generates the first light corresponding to a radiation emitted through the substrate and is configured to include the columnar crystals is laminated on the other surface of the substrate having the first photoelectric conversion element, which has one surface from which a radiation is emitted and the other surface from which at least one of the first light and the second light is emitted and which generates electric charges corresponding to the light, and the first switching element for reading the electric charges generated by the first photoelectric conversion element. In addition, the second phosphor layer which generates the second light corresponding to a radiation emitted through the first phosphor layer and has different energy characteristics of absorbed radiations from the first phosphor layer is laminated on the surface of the first phosphor layer not facing the substrate.

That is, in the present invention, since the substrate, the first phosphor layer, and the second phosphor layer are laminated in this order, and a radiation is emitted from the substrate side, the surface of the first phosphor layer laminated on the substrate emits light more strongly than the other surface does. Accordingly, since the light emitting position of the first phosphor layer with respect to the substrate is close compared with a case where the radiation is emitted from the second phosphor layer side, the resolution of a radiological image obtained by radiographing can be increased. As a result, the quality of the obtained radiological image can be improved.

In addition, in the present invention, the second light generated by the second phosphor layer is effectively guided to the substrate due to the light guiding function by columnar crystals of the first phosphor layer. Also in this point, the quality of a radiological image can be improved.

In addition, in the present invention, a radiation which cannot be absorbed by the first phosphor layer can be absorbed by the second phosphor layer. Therefore, the first phosphor layer configured to include relatively high-cost columnar crystals can be made thin. As a result, an increase in cost can be suppressed.

Thus, in the radiation detector according to the first aspect of the present invention, the first phosphor layer configured to include the columnar crystals which generates the first light corresponding to a radiation emitted through the substrate is laminated on the other surface of the substrate having the first photoelectric conversion element, which has one surface from which a radiation is emitted and the other surface from which at least one of the first light and the second light is emitted and which generates electric charges corresponding to the light, and the first switching element for reading the electric charges generated by the first photoelectric conversion element. In addition, the second phosphor layer which generates the second light corresponding to a radiation emitted through the first phosphor layer and has different energy characteristics of absorbed radiations from the first phosphor layer is laminated on the surface of the first phosphor layer not facing the substrate. Therefore, the quality of an obtained radiological image can be improved without causing an increase in cost.

Moreover, according to a second aspect of the present invention, in the radiation detector according to the first aspect of the present invention, the first phosphor layer may have non-columnar crystals formed on a surface laminated on the substrate. In this case, the adhesion between the substrate and the first phosphor layer can be improved.

Moreover, according to a third aspect of the present invention, in the radiation detector according to the first or second aspect of the present invention, a reflective layer may be laminated on an opposite surface of the second phosphor layer to a surface laminated on the first phosphor layer. In this case, light generated by each of the first and second phosphor layers can be efficiently condensed to the substrate side.

Moreover, according to a fourth aspect of the present invention, the radiation detector according to the first aspect of the present invention may further include a second substrate which is provided on an opposite surface of the second phosphor layer to a surface laminated on the first phosphor layer and which has a second photoelectric conversion element, which generates electric charges corresponding to the second light generated by the second phosphor layer, and a second switching element for reading the electric charges generated by the second photoelectric conversion element. In this case, compared with a case where the second substrate is not provided, light generated by the second phosphor layer can be used efficiently.

Moreover, according to a fifth aspect of the present invention, the radiation detector according to the first aspect of the present invention may further include a second substrate which is provided between the first and second phosphor layers and which has a second photoelectric conversion element, which generates electric charges corresponding to the second light generated by the second phosphor layer, and a second switching element for reading the electric charges generated by the second photoelectric conversion element. In this case, compared with a case where the second substrate is not provided, light generated by the second phosphor layer can be used efficiently.

In particular, according to a sixth aspect of the present invention, in the radiation detector according to the fifth aspect of the present invention, a side of the first phosphor layer laminated on the substrate may be distal ends of the columnar crystals. In this case, compared with a case where the distal ends of the columnar crystals are laminated on the second phosphor layer, the quality of the obtained radiological image can be further improved.

Moreover, according to a seventh aspect of the present invention, in the radiation detector according to the fifth or sixth aspect of the present invention, a reflective layer may be laminated on an opposite surface of the second phosphor layer to a surface laminated on the second substrate. In this case, light generated by the second phosphor layer can be efficiently condensed to the second substrate side.

Moreover, according to an eighth aspect of the present invention, in the radiation detector according to any one of the fifth to seventh aspects of the present invention, the photoelectric conversion element of the second substrate may be configured to include an organic photoelectric conversion material. In this manner, noise can be effectively suppressed.

Moreover, according to a ninth aspect of the present invention, in the radiation detector according to any one of the fifth to eighth aspects of the present invention, at least one of the substrate and the second substrate may be a flexible substrate. In this case, even if there is a relatively large difference in the heights of the distal ends of columnar crystals of the first phosphor layer, the adhesion between the substrate and the first phosphor layer can be improved.

Moreover, according to a tenth aspect of the present invention, in the radiation detector according to any one of the first to ninth aspects of the present invention, distal ends of the columnar crystals in the first phosphor layer may be formed to be flat. In this case, the adhesion between the first and second phosphor layers can be improved.

Moreover, according to an eleventh aspect of the present invention, in the radiation detector according to any one of the first to tenth aspects of the present invention, the second phosphor layer may be configured to include a material with a larger atomic number than an atomic number of an element which forms the columnar crystals.

Moreover, according to a twelfth aspect of the present invention, in the radiation detector according to any one of the first to eleventh aspects of the present invention, the first phosphor layer may be configured to include columnar crystals of CsI, and the second phosphor layer may be configured to include GOS.

Moreover, according to a seventeenth aspect of the present invention, the radiation detector according to any one of the first to sixteenth aspects of the present invention may further include a buffering layer which is interposed between distal ends of columnar crystals and an object to be laminated on the distal ends, is directly laminated at least on the distal ends, and is transparent to visible light. In this case, even when an abnormal protrusion is generated on distal ends of the columnar crystals, the protrusion can be protected.

Moreover, according to a nineteenth aspect of the present invention, the radiation detector according to any one of the first to eighteenth aspects of the present invention may further include a half mirror layer which is interposed between the first phosphor layer and the second phosphor layer, reflects light from the first phosphor layer, and allows the light to be transmitted from the second phosphor layer. In this case, since it is possible that the light generated in the first phosphor layer is allowed to travel by only the columnar crystals of the first phosphor layer, a radiological image with less blurring can be obtained with the light guiding effect of the columnar crystals.

In addition, in order to achieve the above-described object, according to a twenty-first aspect of the present invention, there is provided a radiological image radiographing apparatus including: the radiation detector according to any one of the first to twelfth aspects of the present invention; and a generation unit for generating image information indicated by electric charges read from the radiation detector.

In the radiological image radiographing apparatus according to the twenty-first aspect of the present invention, image information indicated by electric charges read from the radiation detector of the present invention is generated by the generation unit.

Thus, since the radiological image radiographing apparatus according to the twenty-first aspect of the present invention includes the radiation detector of the present invention, the quality of the obtained radiological image can be improved without causing an increase in cost.

In addition, in order to achieve the above-described object, according to a twenty-third aspect of the present invention, there is provided a radiological image radiographing apparatus including: the radiation detector according to the fourth or fifth aspect of the present invention; and a generation unit for generating new image information by adding, for each corresponding pixel, the image information indicated by electric charges read from the substrate and the second substrate provided in the radiation detector.

In the radiological image radiographing apparatus according to the twenty-third aspect of the present invention, new image information is generated by adding, for each corresponding pixel, the image information indicated by electric charges read from the substrate and the second substrate provided in the radiation detector according to the fourth or fifth aspect of the present invention.

Thus, since the radiological image radiographing apparatus according to the twenty-third aspect of the present invention includes the radiation detector of the present invention, the quality of the obtained radiological image can be improved without causing an increase in cost. In addition, according to the present invention, new image information is generated by adding, for each corresponding pixel, the image information indicated by electric charges read from the substrate and the second substrate. As a result, the sensitivity of the entire radiation detector can be improved.

According to the present invention, the effect can be obtained in which the quality of an obtained radiological image can be improved without causing an increase in cost.

BRIEF DESCRIPTION OF THE DRAWINGS

FIG. 14 is a flow chart showing the process flow of an image information transmission processing program according to the second embodiment.

DESCRIPTION OF THE PREFERRED EMBODIMENTS

Hereinafter, embodiments of the present invention will be described in detail with reference to the accompanying drawings.

First Embodiment

First, the configuration of an indirect conversion-type radiation detector 20 according to the present embodiment will be described.

Figure 1:
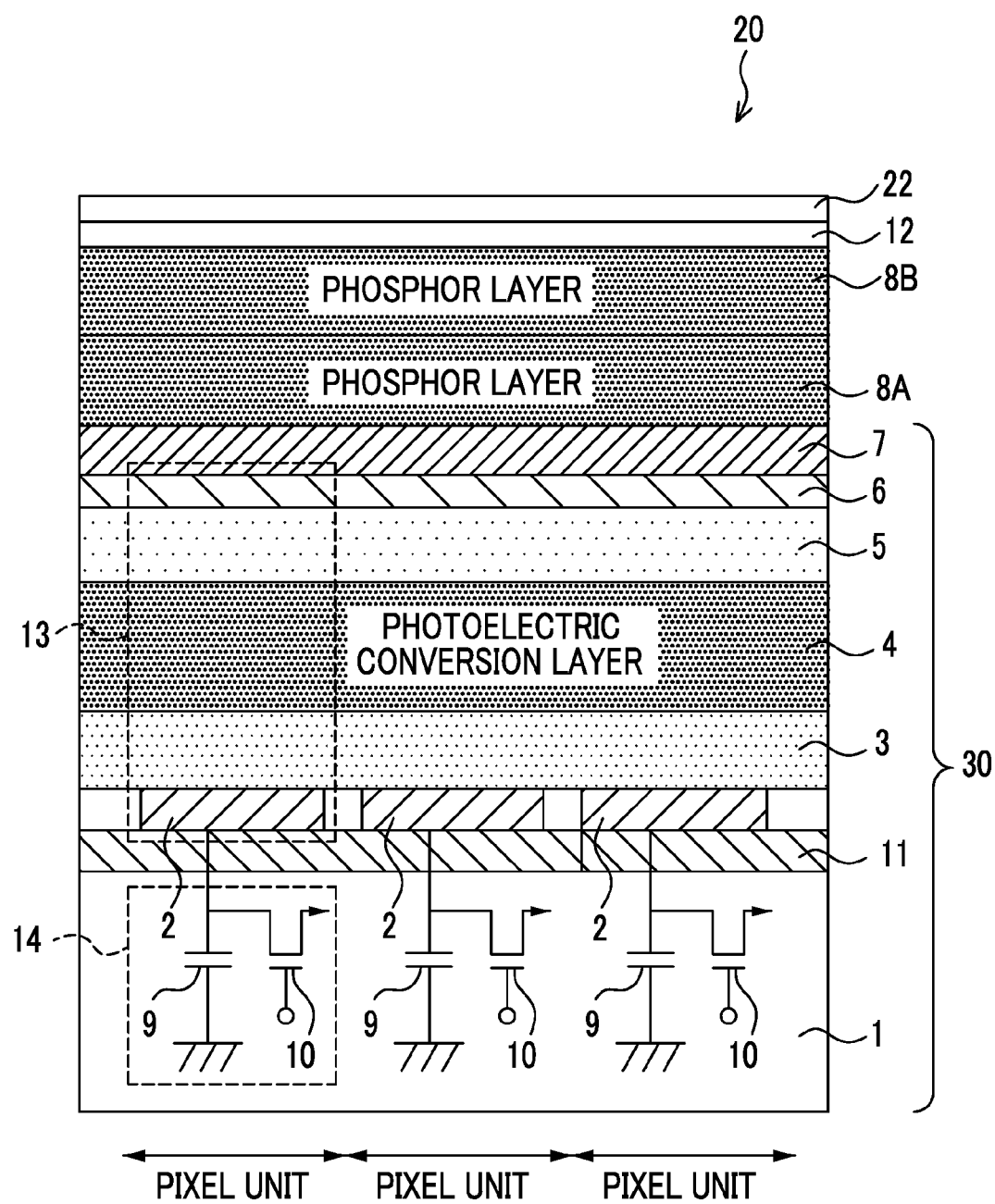
FIG. 1 is a cross-sectional view showing the schematic configuration of three pixel units of a radiation detector according to a first embodiment.

FIG. 1 is a schematic cross-sectional view showing the configuration of three pixel units of the radiation detector 20 which is an embodiment of the present invention.

In the radiation detector 20, a signal output section 14 (first switching element), a sensor section 13 (first photoelectric conversion element), a transparent insulating layer 7, a scintillator 8A (first phosphor layer), a scintillator 8B (second phosphor layer), a reflective layer 12, and a base 22 are laminated on an insulating substrate 1 in this order. A pixel unit is formed by the signal output sections 14 and the sensor sections 13. A plurality of pixel units are arrayed on the substrate 1, and each pixel unit is configured such that the signal output section 14 and the sensor section 13 overlap each other. In addition, in the present embodiment, a TFT substrate 30 is configured by forming the signal output section 14, the sensor section 13, and the transparent insulating layer 7 in this order on the substrate 1.

The scintillator 8A is formed of columnar crystals on the sensor section 13 with the transparent insulating layer 7 interposed therebetween, and is formed by depositing a phosphor which converts a radiation incident from the lower side (substrate 1 side) into first light and emits the first light. By providing such a scintillator 8A, a radiation transmitted through a subject is absorbed to emit light.

It is preferable that the wavelength range of the first light emitted from the scintillator 8A be a visible light range (wavelength of 360 nm to 830 nm). In order for the radiation detector 20 to be able to perform monochrome imaging, it is more preferable to include a green wavelength range.

As a phosphor used as the scintillator 8A, specifically, a phosphor including cesium iodide (CsI) is preferably used in the case of imaging using an X-ray as a radiation. Especially, it is preferable to use CsI:Tl whose emission spectrum at the time of X-ray irradiation is in a rage of 420 nm to 700 nm, for example. In addition, the peak emission wavelength of CsI:Tl in the visible light range is 565 nm.

Figure 2:
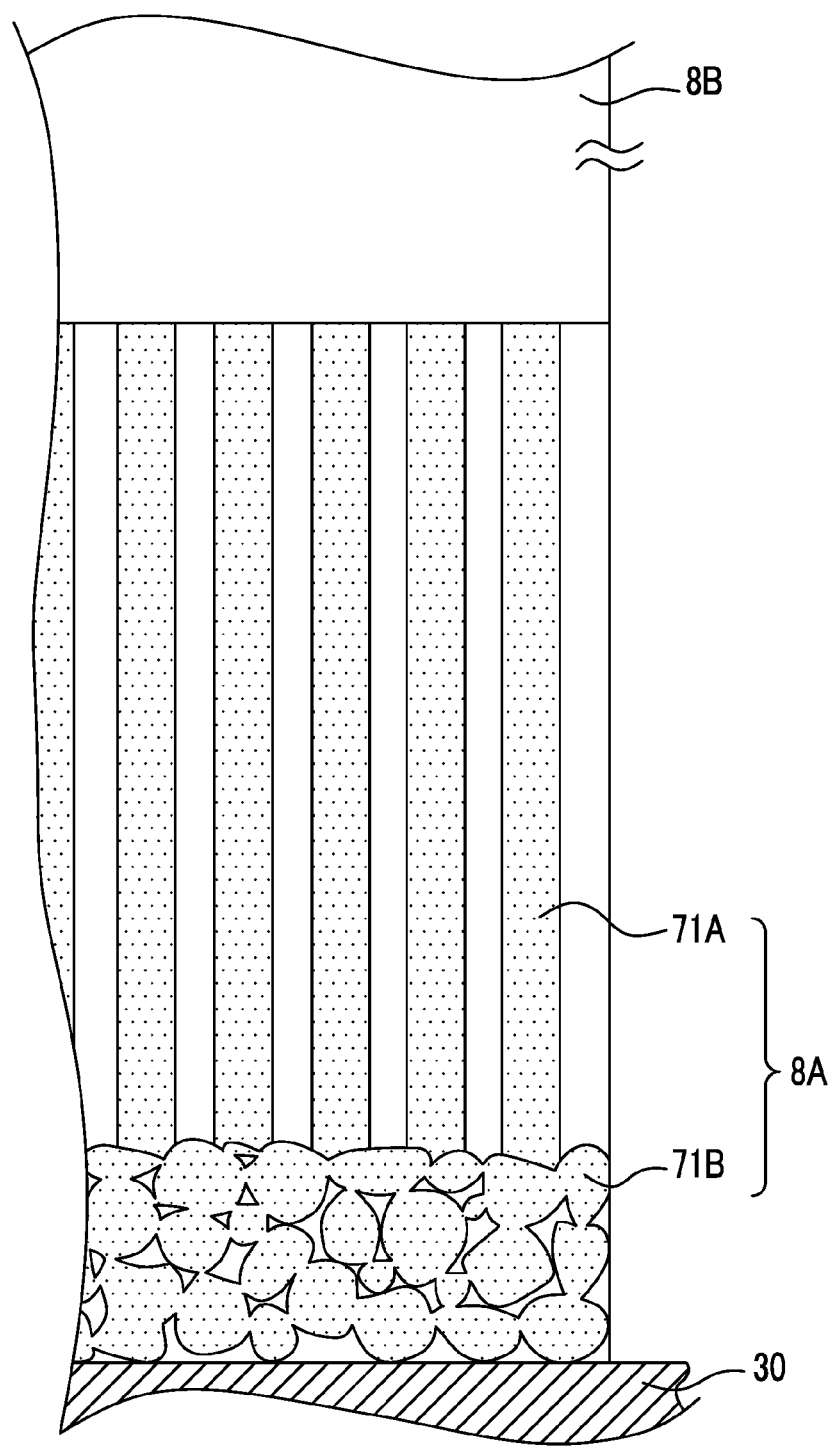
FIG. 2 is a schematic view showing an example of the crystal configuration of a scintillator according to the embodiment.

Moreover, in the present embodiment, as an example, as shown in FIG. 2, the scintillator 8A has a configuration in which a non-columnar portion formed of non-columnar crystals 71B is formed on the radiation incidence/light emission side (TFT substrate 30B side) and a columnar portion formed of columnar crystals 71A is formed on the opposite side to the radiation incidence side of the scintillator 8A, and a material including CsI is used as the scintillator 8A. By vapor-depositing the material directly on the TFT substrate 30, the scintillator 8A in which the columnar portion and the non-columnar portion are formed is obtained. In addition, in the scintillator 8A according to the present embodiment, the average diameter of the columnar crystals 71A is approximately uniform along the longitudinal direction of the columnar crystals 71A.

As described above, by forming the scintillator 8A with a columnar portion, the first light generated in the scintillator 8A propagates through the columnar crystals 71A and is emitted to the TFT substrate 30 through the non-columnar crystals 71B. Therefore, since diffusion of light emitted to the TFT substrate 30 side is suppressed, a decrease in the sharpness of a radiological image obtained as a result is suppressed. In addition, the first light propagating to the distal end side of the columnar crystals 71A of the scintillator 8A is transmitted through the scintillator 8B and is then reflected by the reflective layer 12, contributing to an increase in the amount of light received by the TFT substrate 30.

In addition, by bringing the porosity of the non-columnar portion close to 0 (zero), reflection of light by the non-columnar portion can be preferably suppressed. In addition, it is preferable that the non-columnar portion be made as thin as possible (approximately 10 μm).

On the other hand, the scintillator 8B is formed so as to have different energy characteristics of absorbed radiations from the scintillator 8A, and is formed by depositing a phosphor which converts a radiation incident from the lower side (substrate 1 side) into second light and emits the second light. By providing such a scintillator 8B, a radiation transmitted through the scintillator 8A is absorbed to emit light. Preferably, the wavelength range of the second light emitted from the scintillator 8B is also a visible light range.

As a phosphor used as the scintillator 8B, specifically, a phosphor including GOS is preferably used in the case of imaging using an X-ray as a radiation. Especially, it is preferable to use GOS:Tb. In addition, the peak emission wavelength of GOS:Tb in the visible light range is 550 nm.

Figure 3:
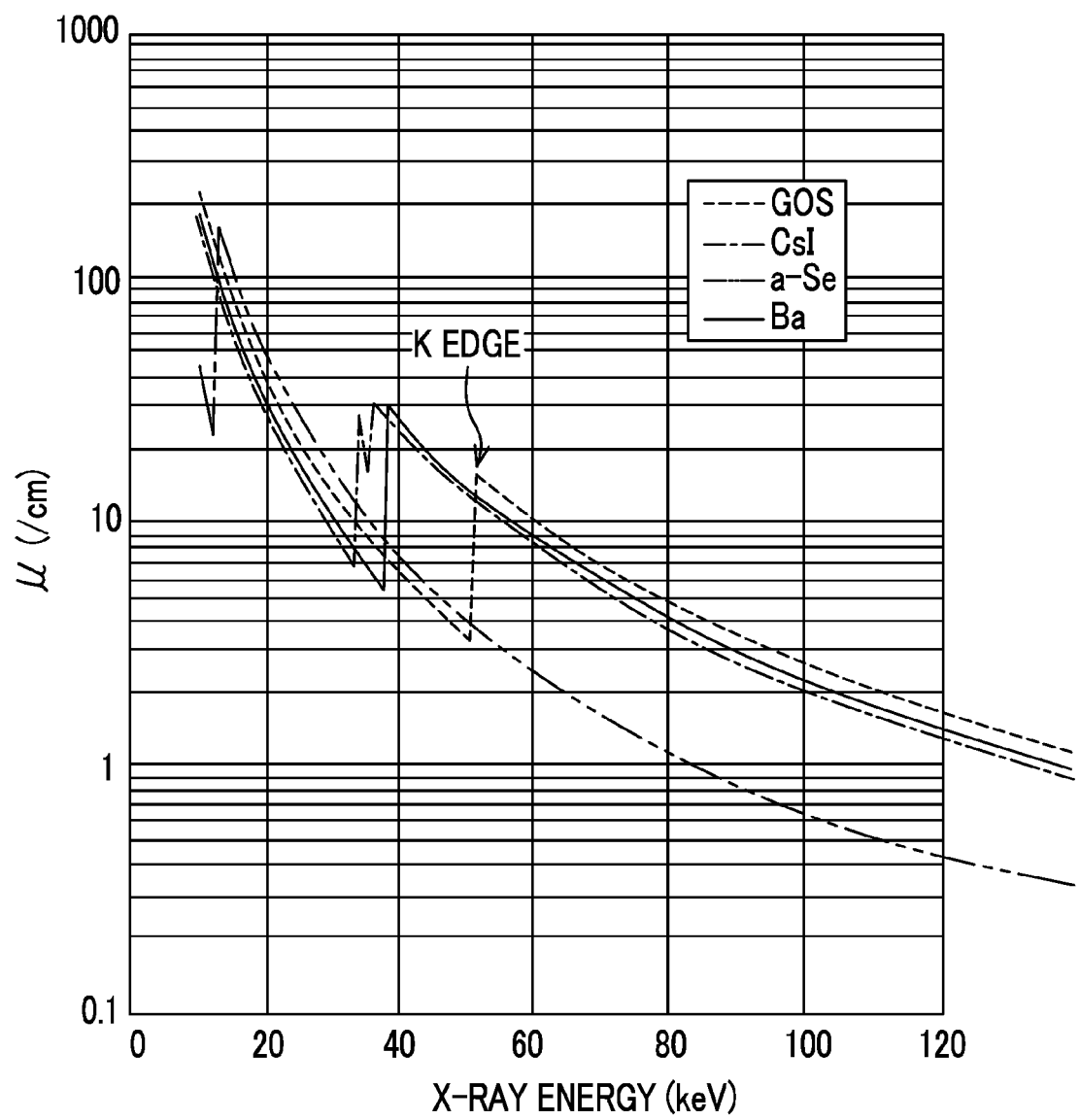
FIG. 3 is a graph showing the X-ray absorption characteristics of various materials.

FIG. 3 shows the X-ray absorption characteristics of various materials.

As shown in FIG. 3, atomic numbers of elements making up the GOS are larger than those making up the CsI. For example, in the case of GOS:Pr, a K-edge is present near 50 [KeV]. Accordingly, since the high-energy X-ray absorption rate of the GOS is higher than that of the CsI which is columnar crystals, a radiation which cannot be absorbed by the CsI can be absorbed effectively. In addition, the K-edge in the GOS changes with a doping material. For example, the K-edge of GOS:Tb is approximately 60 [KeV]. In addition, the atomic number referred to herein is an effective atomic number calculated in consideration of the composition ratio of the scintillator.

In addition, the reflective layer 12 reflects visible light. Accordingly, by forming the reflective layer 12, the first light generated in the scintillator 8A and the second light generated in the scintillator 8B can be more efficiently guided to the sensor section 13. As a result, the sensitivity is improved. Any of a sputtering method, a vapor deposition method, and a coating method may be used as a method of forming the reflective layer 12. As the reflective layer 12, it is preferable to use materials with a high reflectance in the emission wavelength region of the used scintillators 8A and 8B, such as Au, Ag, Cu, Al, Ni, and Ti. For example, when the scintillator 8B is GOS:Tb, it is preferable to use Ag, Al, or Cu which has a high reflectance at the wavelength of 400 to 600 nm. Regarding the thickness, the reflectance is not obtained if the thickness is less than 0.01 μm, and the effect by the improvement in reflectance is not obtained further even if the thickness exceeds 3 μm. Accordingly, the preferable thickness is 0.01 to 3 μm.

In addition, in the present embodiment, the TFT substrate 30 is disposed on the irradiation surface side of each scintillator, and the method of disposing each scintillator and the TFT substrate 30 so as to satisfy such a positional relationship is called "Irradiation Side Sampling (ISS)". Since the radiation incidence side of the scintillator emits light more strongly, the TFT substrate 30 and the light emitting position of the scintillator are brought close to each other in the irradiation side sampling (ISS) in which the TFT substrate 30 is disposed on the radiation incidence side of the scintillator, compared with "Penetration Side Sampling (PSS)" in which the TFT substrate 30 is disposed on the opposite side to the radiation incidence side of the scintillator. Accordingly, the resolution of a radiological image obtained by radiographing is high, and the amount of received light in the TFT substrate 30 is increased. As a result, the sensitivity of the radiological image is improved.

On the other hand, the sensor section 13 has an upper electrode 6, a lower electrode 2, and a photoelectric conversion layer 4 disposed between the upper and lower electrodes. The photoelectric conversion layer 4 is formed of an organic photoelectric conversion material which absorbs the first light emitted from the scintillator 8A and the second light emitted from the scintillator 8B to generate electric charges.

The upper electrode 6 is preferably formed of a conductive material which is transparent to at least the emission wavelength of the scintillator, since it is necessary to make the first and second light beams generated by the scintillators incident on the photoelectric conversion layer 4. Specifically, it is preferable to use a transparent conducting oxide (TCO) which has a high transmittance for visible light and has a low resistance value. In addition, although a thin metal film, such as Au, may also be used as the upper electrode 6, the resistance value tends to increase when a transmittance of 90% or more needs to be obtained. For this reason, the TCO is preferable. For example, ITO, IZO, AZO, FTO, $SnO_2$, $TiO_2$, and $ZnO_2$ may be preferably used. Among these, ITO is the most preferable material from the point of view of process simplicity, low resistance, and transparency. In addition, the upper electrode 6 may be a common one-sheet configuration in all pixel units, or a separate upper electrode 6 may be provided in each pixel unit.

The photoelectric conversion layer 4 includes an organic photoelectric conversion material, and absorbs the first light emitted from the scintillator 8A and the second light emitted from the scintillator 8B and generates electric charges corresponding to the absorbed first and second light beams. The photoelectric conversion layer 4 including an organic photoelectric conversion material as described above has an absorption spectrum which is sharp in a visible range. Accordingly, electromagnetic waves other than the light emitted from the scintillators 8A and 8B are hardly absorbed by the photoelectric conversion layer 4. As a result, noise generated when radiations, such as X-rays, are absorbed by the photoelectric conversion layer 4 can be suppressed effectively.

In order to absorb the first and second light beams emitted from the scintillators 8A and 8B most efficiently, it is preferable that the peak absorption wavelength of the organic photoelectric conversion material which forms the photoelectric conversion layer 4 be as close to the peak emission wavelength of each scintillator as possible. Although it is ideal for the peak absorption wavelength of the organic photoelectric conversion material and the peak emission wavelength of each scintillator to be equal, light emitted from each scintillator can be sufficiently absorbed if a difference between both the wavelengths is small. Specifically, it is preferable that the difference between the peak absorption wavelength of the organic photoelectric conversion material and the peak emission wavelength of each scintillator for the radiation be equal to or less than 10 nm. More preferably, the difference is less than 5 nm.

As examples of the organic photoelectric conversion material which can satisfy such conditions, a quinacridone based organic compound and a phthalocyanine based organic compound may be mentioned. For example, the peak absorption wavelength of quinacridone in the visible light range is 560 nm. Accordingly, if quinacridone is used as an organic photoelectric conversion material, CsI:Tl is used as a material of the scintillator 8A, and GOS is used as a material of the scintillator 8B, the difference between the peak wavelengths can be made to fall within 10 nm. As a result, the amount of charges generated in the photoelectric conversion layer 4 can be nearly maximized.

Next, the photoelectric conversion layer 4 applicable to the radiation detector 20 according to the present embodiment will be specifically described.

An electromagnetic wave absorption/photoelectric conversion section in the radiation detector 20 according to the present embodiment may be formed by an organic layer including a pair of electrodes 2 and 6 and the organic photoelectric conversion layer 4 interposed between the electrodes 2 and 6. More specifically, this organic layer may be formed by stacking or mixing of a portion which absorbs electromagnetic waves, a photoelectric conversion portion, an electron transport portion, a hole transport portion, an electron blocking portion, a hole blocking portion, a crystallization preventing portion, an electrode, an interlayer contact improving portion, and the like.

Preferably, the above organic layer contains an organic p-type compound or an organic n-type compound.

The organic p-type semiconductor (compound) is a semiconductor (compound) with a donor property which is mainly represented by an organic compound with a hole transport property, and is called an organic compound with a property prone to donating electrons. More specifically, the organic p-type semiconductor (compound) refers to an organic compound with smaller ionization potential when two organic materials are used in a state where they are in contact with each other. Therefore, as an organic compound with a donor property, any organic compound may be used if it is an organic compound with an electron-donating property.

The organic n-type semiconductor (compound) is a semiconductor (compound) with an acceptor property which is mainly represented by an organic compound with an electron transport property, and is called an organic compound with a property of easily accepting electrons. More specifically, the organic n-type semiconductor (compound) refers to an organic compound with larger electron affinity when two organic materials are used in a state where they are in contact with each other. Therefore, as an organic compound with an acceptor property, any organic compound may be used if it is an organic compound with an electron-accepting property.

Materials applicable as the organic p-type semiconductor and the organic n-type semiconductor and the configuration of the photoelectric conversion layer 4 are disclosed in detail in JP2009-32854A. Accordingly, explanation thereof will be omitted.

The thickness of the photoelectric conversion layer 4 is preferably as large as possible from the point of view of absorption of the first light from the scintillator 8A and the second light from the scintillator 8B. However, if the thickness of the photoelectric conversion layer 4 is equal to or greater than a certain value, the strength of the electric field generated in the photoelectric conversion layer 4 is reduced due to the bias voltage applied from both ends of the photoelectric conversion layer 4 and as a result, it is not possible to collect electric charges. For this reason, the thickness of the photoelectric conversion layer 4 is preferably 30 nm or more and 300 nm or less, more preferably 50 nm or more 250 nm or less, and most preferably 80 nm or more and 200 nm or less.

In addition, in the radiation detector 20 shown in FIG. 1, the photoelectric conversion layer 4 is a common one-sheet configuration in all pixel units. However, a separate photoelectric conversion layer 4 may be provided in each pixel unit.

The lower electrode 2 is assumed to be a thin film divided for each pixel unit. The lower electrode 2 may be formed of a transparent or opaque conductive material. Aluminum, silver, and the like may be appropriately used for the lower electrode 2.

The thickness of the lower electrode 2 may be set to 30 nm or more and 300 nm or less, for example.

In the sensor section 13, a predetermined bias voltage may be applied between the upper electrode 6 and the lower electrode 2 in order to move one of two types of electric charges (holes and electrons) generated in the photoelectric conversion layer 4 to the upper electrode 6 and move the other one to the lower electrode 2. In the radiation detector 20 according to the present embodiment, it is assumed that a wiring line is connected to the upper electrode 6 and a bias voltage is applied to the upper electrode 6 through the wiring line. In addition, although the polarity of the bias voltage is determined such that electrons generated in the photoelectric conversion layer 4 move to the upper electrode 6 and holes move to the lower electrode 2, the polarity may be reversed.

The sensor section 13 of each pixel unit may include at least the lower electrode 2, the photoelectric conversion layer 4, and the upper electrode 6. However, in order to suppress an increase in a dark current, it is preferable to provide at least either an electron blocking layer 3 or a hole blocking layer 5. More preferably, both the electron blocking layer 3 and the hole blocking layer 5 are provided.

The electron blocking layer 3 can be provided between the lower electrode 2 and the photoelectric conversion layer 4. Accordingly, when a bias voltage is applied between the lower electrode 2 and the upper electrode 6, a situation can be suppressed in which electrons are injected from the lower electrode 2 to the photoelectric conversion layer 4 and this increases a dark current.

An organic material with an electron-donating property may be used for the electron blocking layer 3.

The material used for the electron blocking layer 3 in practice may be selected according to a material of the adjacent electrode, a material of the adjacent photoelectric conversion layer 4, or the like. Preferably, the material used for the electron blocking layer 3 has an electron affinity (Ea), which is larger by 1.3 eV or more than the work function (Wl) of the material of the adjacent electrode, and has the same ionization potential (Ip) as the material of the adjacent photoelectric conversion layer 4 or a smaller Ip than the material of the adjacent photoelectric conversion layer 4. Since materials applicable as the organic material with an electron-donating property are disclosed in detail in JP2009-32854A, explanation thereof will be omitted. In addition, the photoelectric conversion layer 4 may also be formed so as to further contain fullerene or carbon nanotubes.

In order to reliably obtain the effect of suppressing a dark current and to prevent the degradation of the photoelectric conversion efficiency of the sensor section 13, the thickness of the electron blocking layer 3 is preferably 10 nm or more and 200 nm or less, more preferably 30 nm or more and 150 nm or less, and most preferably 50 nm or more 100 nm or less.

The hole blocking layer 5 can be provided between the photoelectric conversion layer 4 and the upper electrode 6. Accordingly, when a bias voltage is applied between the lower electrode 2 and the upper electrode 6, a situation can be suppressed in which holes are injected from the upper electrode 6 to the photoelectric conversion layer 4 and this increases a dark current.

An organic material with an electron-accepting property may be used for the hole blocking layer 5.

In order to reliably obtain the effect of suppressing a dark current and to prevent the degradation of the photoelectric conversion efficiency of the sensor section 13, the thickness of the hole blocking layer 5 is preferably 10 nm or more and 200 nm or less, more preferably 30 nm or more and 150 nm or less, and most preferably 50 nm or more 100 nm or less.

The material used for the hole blocking layer 5 in practice may be selected according to a material of the adjacent electrode, a material of the adjacent photoelectric conversion layer 4, or the like. Preferably, the material used for the hole blocking layer 5 has an ionization potential (Ip), which is larger by 1.3 eV or more than the work function (Wf) of the material of the adjacent electrode, and the same electron affinity (Ea) as the material of the adjacent photoelectric conversion layer 4 or a larger Ea than the material of the adjacent photoelectric conversion layer 4. Since materials applicable as the organic material with an electron-accepting property are disclosed in detail in JP2009-32854A, explanation thereof will be omitted.

In addition, when a bias voltage is set such that holes of electric charges generated in the photoelectric conversion layer 4 move to the lower electrode 2 and electrons move to the upper electrode 6, it is preferable to reverse the positions of the electron blocking layer 3 and the hole blocking layer 5. In addition, both the electron blocking layer 3 and the hole blocking layer 5 may not be provided. If one of the layers is provided, the effect of suppressing a dark current can be obtained to some extent.

The signal output section 14 is formed on the surface of the substrate 1 below the lower electrode 2 of each pixel unit.

Figure 4:
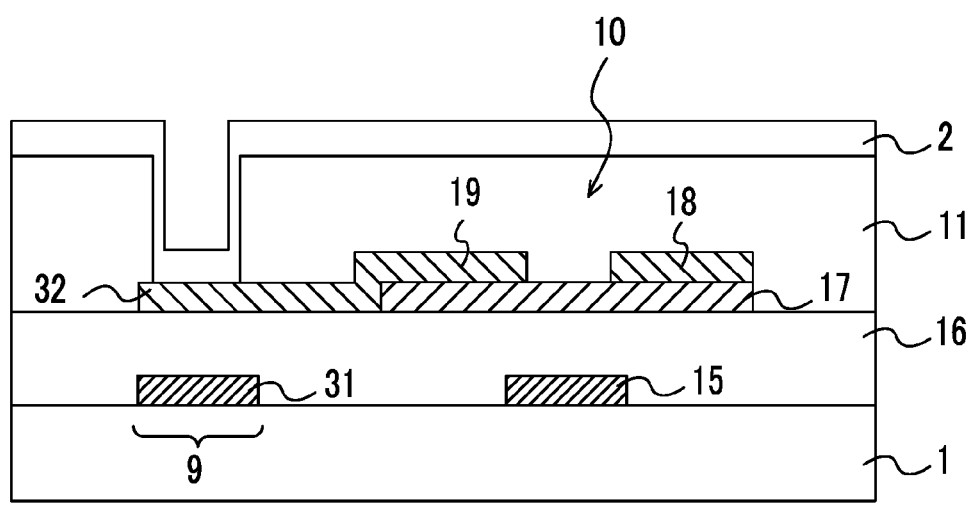
FIG. 4 is a cross-sectional view showing the schematic configuration of a signal output section of one pixel unit of the radiation detector according to the embodiment.

FIG. 4 shows the schematic configuration of the signal output section 14.

A capacitor 9, which accumulates electric charges having moved to the lower electrode 2, and a field effect thin film transistor (hereinafter, simply referred to as a "thin film transistor") 10, which converts the electric charges accumulated in the capacitor 9 into an electric signal and outputs the electric signal, are formed corresponding to the lower electrode 2. The region where the capacitor 9 and the thin film transistor 10 are formed has a portion overlapping the lower electrode 2 in plan view. By adopting such a configuration, the signal output section 14 and the sensor section 13 in each pixel unit overlap each other in the thickness direction. In addition, in order to minimize the plane area of the radiation detector 20 (pixel unit), it is preferable that the region where the capacitor 9 and the thin film transistor 10 are formed be completely covered by the lower electrode 2.

The capacitor 9 is electrically connected to the corresponding lower electrode 2 through a wiring line of a conductive material which is formed so as to pass through an insulating layer 11 provided between the substrate 1 and the lower electrode 2. Accordingly, electric charges collected in the lower electrode 2 can be moved to the capacitor 9.

The thin film transistor 10 is formed by laminating a gate electrode 15, a gate insulating layer 16, and an active layer (channel layer) 17 and forming a source electrode 18 and a drain electrode 19 further on the active layer 17 with a predetermined distance therebetween.

For example, the active layer 17 may be formed of amorphous silicon, amorphous oxide, an organic semiconductor material, carbon nanotubes, or the like. In addition, materials which form the active layer 17 are not limited to these.

As amorphous oxides which can form the active layer 17, an oxide containing at least one of In, Ga, and Zn (for example, an In—O based oxide) is preferably used, an oxide containing at least two of In, Ga, and Zn (for example, an In—Zn—O based oxide, an In—Ga—O based oxide, and a Ga—Zn—O based oxide) is more preferable, and an oxide containing In, Ga, and Zn is most preferable. As an In—Ga—Zn—O based amorphous oxide, an amorphous oxide whose composition in the crystalline state is expressed as $InGaO_3(ZnO)_m$ (m is a natural number of 6 or less) is preferable. In particular, $InGaZnO_4$ is more preferable. In addition, materials which can form the active layer 17 are not limited to these.

As organic semiconductor materials which can form the active layer 17, a phthalocyanine compound, pentacene, vanadyl phthalocyanine, and the like may be mentioned. However, the organic semiconductor materials which can form the active layer 17 are not limited to these. In addition, the configuration of the phthalocyanine compound is disclosed in detail in JP2009-212389A. Accordingly, explanation thereof will be omitted.

If the active layer 17 of the thin film transistor 10 is formed of an amorphous oxide, an organic semiconductor material, or carbon nanotubes, a radiation such as an X-ray is not absorbed or a very small amount of radiation is absorbed even if it is absorbed. Therefore, the generation of noise in the signal output section 14 can be effectively suppressed.

In addition, when the active layer 17 is formed of carbon nanotubes, the switching speed of the thin film transistor 10 can be increased, and the thin film transistor 10 whose light absorbance in the visible light range is low can be formed. In addition, when the active layer 17 is formed of carbon nanotubes, the performance of the thin film transistor 10 is significantly reduced even if a very small amount of metallic impurities are mixed into the active layer 17. Therefore, it is necessary to form extremely high-purity carbon nanotubes by separation and extraction using centrifugation or the like.

Here, all of the amorphous oxides, the organic semiconductor materials, the carbon nanotubes, and organic photoelectric conversion materials described above may be deposited at low temperature. Therefore, as the substrate 1, a flexible substrate such as plastic, aramid, and a bio-nano fiber may also be used without being limited to highly heat-resistant substrates, such as a semiconductor substrate, a quartz substrate, and a glass substrate. Specifically, flexible substrates formed of polyester such as polyethylene terephthalate, polybutylene, and polyethylene naphthalate, polystyrene, polycarbonate, polyether sulfone, polyarylate, polyimide, polycycloolefin, norbornene resin, and poly(chlorotrifluoroethylene), can be used. If such a flexible substrate formed of plastic is used, the weight can be reduced. This is advantageous in carriage, for example.

In addition, an insulating layer for ensuring insulation, a gas barrier layer for preventing the transmission of moisture or oxygen, an undercoat layer for improving the flatness or the adhesion to an electrode, and the like may be provided on the substrate 1.

In the case of aramid, the high-temperature process at 200° or higher can be applied. Accordingly, a transparent electrode material can be cured at high temperature to reduce the resistance. In addition, aramid can allow automatic mounting of driver ICs, including the solder reflow process. In addition, since the thermal expansion coefficient of aramid is close to that of an ITO (indium tin oxide) or a glass substrate, there is little warping after manufacture. Accordingly, resistance to cracking is high. In addition, aramid can form a thin substrate compared with a glass substrate or the like. In addition, the substrate 1 may also be formed by laminating an ultra-thin glass substrate and aramid.

A bio-nano fiber is formed by mixing cellulose microfibril bundles (bacterial cellulose) made by bacteria (Acetobacter xylinum) with a transparent resin. The cellulose microfibril bundle has a width of 50 nm and a size equivalent to 1/10 of the visible light wavelength and also has high strength, high elasticity, and low thermal expansion. By impregnating bacterial cellulose with a transparent resin, such as acrylic resin or epoxy resin, and curing it, the bio-nano fiber which has an optical transmittance of approximately 90% at the wavelength of 500 nm while containing 60% to 70% fibers can be obtained. Since the bio-nano fiber has a low thermal expansion coefficient (3 ppm to 7 ppm) comparable to silicon crystal, strength (460 MPa) comparable to steel, and high elasticity (30 GPa) and is also flexible, the substrate 1 which is thinner than a glass substrate or the like can be formed.

In the meantime, in the radiation detector 20 according to the present embodiment, the scintillator 8A is directly formed on the TFT substrate 30 by vapor deposition as described above. However, the radiation detector 20 may be manufactured by various methods without being limited to this. Table 1 shows four examples of a method of manufacturing the radiation detector 20.

TABLE 1

| Manufacturing method | Scintillator 8A | Interface structure | Scintillator 8B |
|---|---|---|---|
| First pattern | Direct vapor deposition | Bonding | Coating |
| Second pattern | Direct vapor deposition | Pressing + pouch of entire radiation detector | Coating |
| Third pattern | Indirect vapor deposition + TFT substrate bonding, peeling off of vapor-deposited substrate | Bonding or pressing | Coating |
| Fourth pattern | Indirect vapor deposition (vapor deposition on scintillator 8B) + TFT substrate bonding | | Coating |

In the manufacturing method of the first pattern, the scintillator 8A is directly formed on the TFT substrate 30 by vapor deposition, and the reflective layer 12 is formed on the base 22 formed of polyethylene terephthalate or the like. Then, the scintillator 8B is formed by coating on the reflective layer 12. Then, the surface (distal side of columnar crystals) of the scintillator 8A not facing the TFT substrate 30 and the surface of the scintillator 8B not facing the reflective layer 12 are bonded to each other using adhesive or the like.

In addition, in the manufacturing method of the second pattern, in the same manner as in the first pattern, the scintillator 8A is directly formed on the TFT substrate 30 by vapor deposition, and the reflective layer 12 is formed on the base 22 formed of polyethylene terephthalate or the like. Then, the scintillator 8B is formed by coating on the reflective layer 12. Then, pouch finishing (lamination) of the entire radiation detector 20 is performed in a state where the surface (distal side of columnar crystals) of the scintillator 8A not facing the TFT substrate 30 and the surface of the scintillator 8B not facing the reflective layer 12 are pressed against each other.

On the other hand, in the manufacturing method of the third pattern, the scintillator 8A is formed on a vapor-deposited substrate (not shown) by vapor deposition, and the reflective layer 12 is formed on the base 22 formed of polyethylene terephthalate or the like in the same manner as in the first and second patterns. Then, the scintillator 8B is formed by coating on the reflective layer 12. Then, the surface (distal side of columnar crystals) of the scintillator 8A not facing the vapor-deposited substrate is bonded to the TFT substrate 30 using adhesive or the like so that the vapor-deposited substrate is peeled off from the scintillator 8A, and the surface of the scintillator 8A not facing the TFT substrate 30 and the surface of the scintillator 8B not facing the reflective layer 12 are bonded to each other using adhesive or the like or are pressed against each other.

In addition, in the manufacturing method of the fourth pattern, in the same manner as in the first to third patterns, the reflective layer 12 is formed on the base 22 formed of polyethylene terephthalate or the like, and then the scintillator 8B is formed by coating on the reflective layer 12. Then, the scintillator 8A is formed on the scintillator 8B by vapor deposition, and the surface (distal side of columnar crystals) of the scintillator 8A not facing the scintillator 8B is bonded to the TFT substrate 30 using adhesive or the like. In the fourth pattern, a non-columnar portion is formed not on the TFT substrate 30 side but on the scintillator 8B side.

In addition, it is preferable to perform control such that the distal end of each columnar portion of the scintillator 8A is as flat as possible. Specifically, this can be realized by controlling the temperature of the vapor-deposited substrate at the end of vapor deposition. For example, when the temperature of the vapor-deposited substrate at the end of vapor deposition is set to 110°, the angle of the distal end is approximately 170°. When the temperature of the vapor-deposited substrate at the end of vapor deposition is set to 140°, the angle of the distal end is approximately 60°. When the temperature of the vapor-deposited substrate at the end of vapor deposition is set to 200°, the angle of the distal end is approximately 70°. When the temperature of the vapor-deposited substrate at the end of vapor deposition is set to 260°, the angle of the distal end is approximately 120°. In addition, this control is disclosed in detail in JP2010-25620A. Accordingly, explanation thereof will be omitted.

Figure 5:
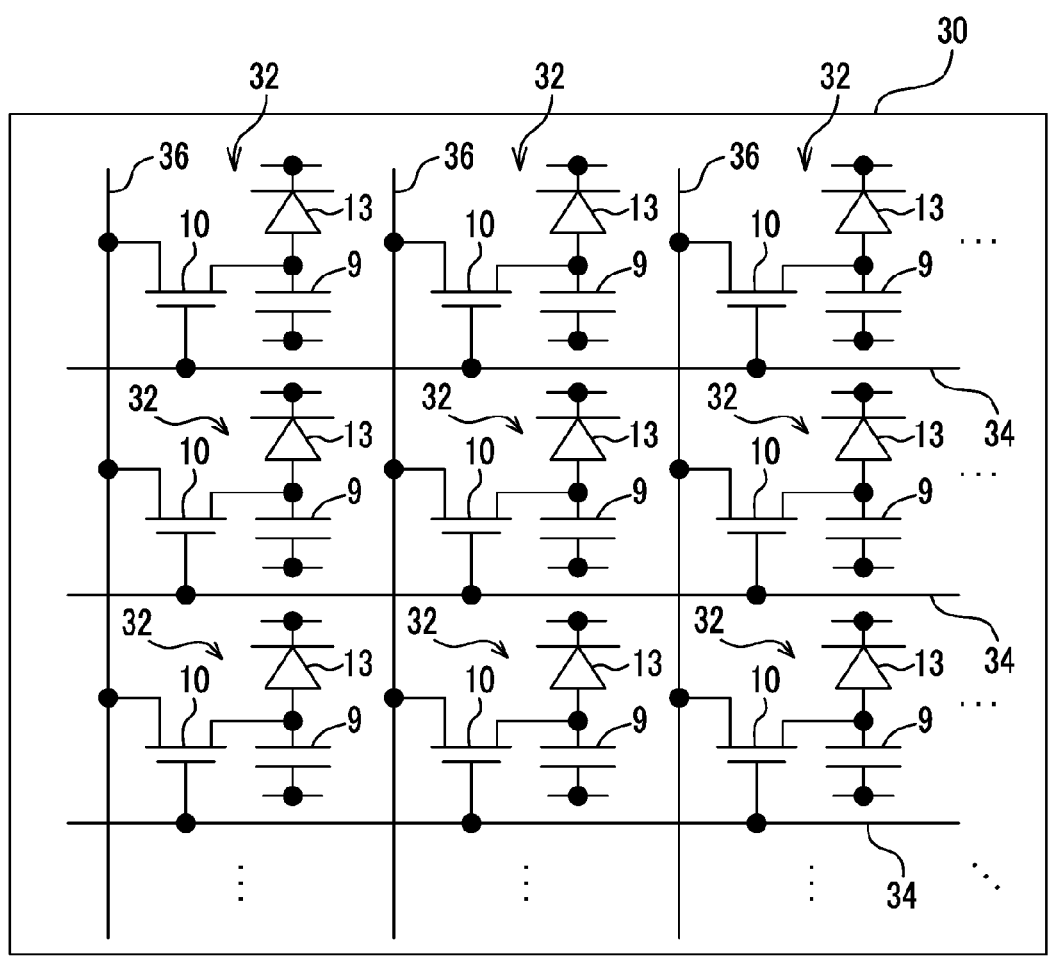
FIG. 5 is a plan view showing the configuration of the radiation detector according to the embodiment.

On the other hand, as shown in FIG. 5, a plurality of pixels 32 each of which is configured to include the sensor section 13, the capacitor 9, and the thin film transistor 10 are provided on the TFT substrate 30A in a two-dimensional manner in a fixed direction (row direction in FIG. 5) and a direction (column direction in FIG. 5) crossing the fixed direction.

In addition, a plurality of gate wiring lines 34 which extend in the above-described fixed direction (row direction) and serve to turn each thin film transistor 10 on and off and a plurality of data wiring lines 36 which extend in the above-described crossing direction (column direction) and serve to read electric charges through the thin film transistor 10 in the ON state are provided in the radiation detector 20.

The radiation detector 20 has a plate shape, and has a quadrilateral shape with four sides on the outer edge in plan view. Specifically, the radiation detector 20 is formed in the rectangular shape.

Figure 6:
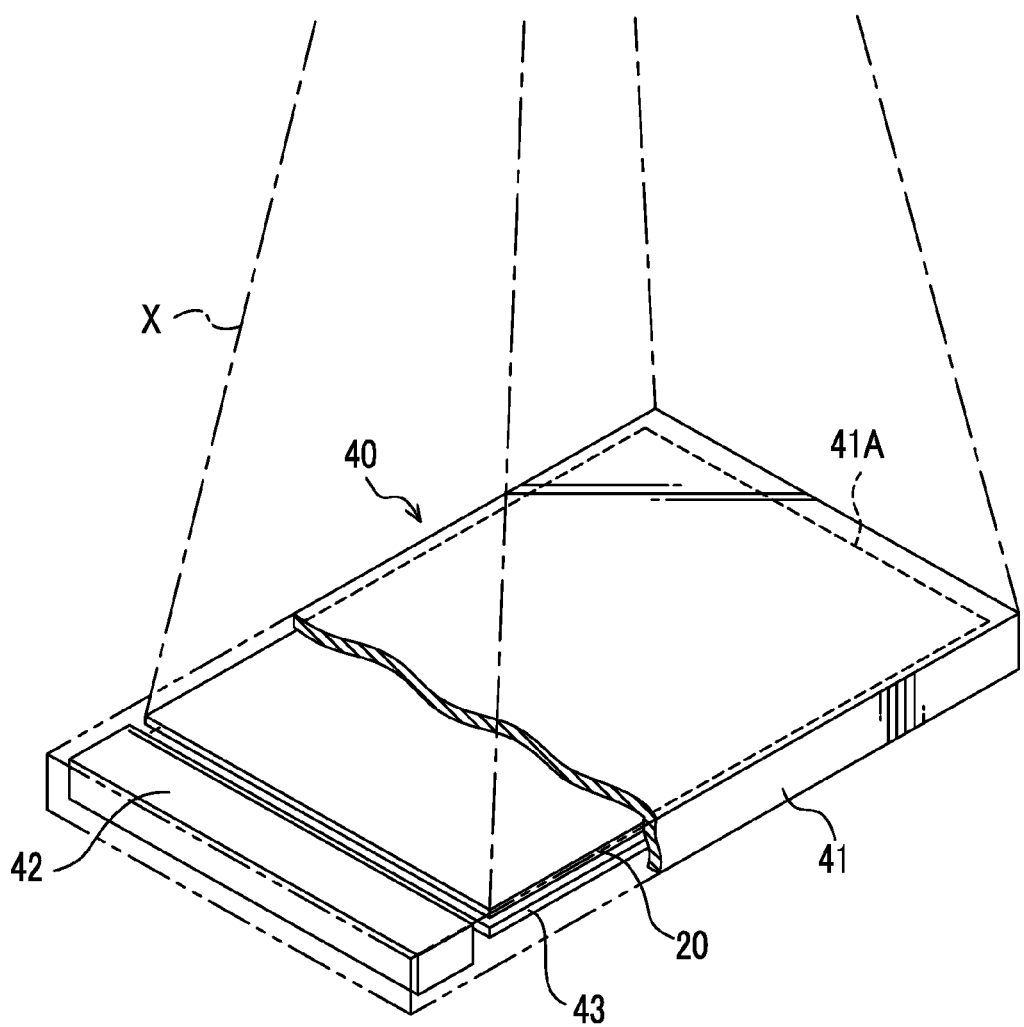
FIG. 6 is a perspective view showing the configuration of an electronic cassette according to the first embodiment.

Next, the configuration of a portable radiological image radiographing apparatus (hereinafter, referred to as an "electronic cassette") 40, which radiographs a radiological image and in which the radiation detector 20 is provided, will be described. FIG. 6 is a perspective view showing the configuration of the electronic cassette 40 according to the present embodiment.

Figure 7:
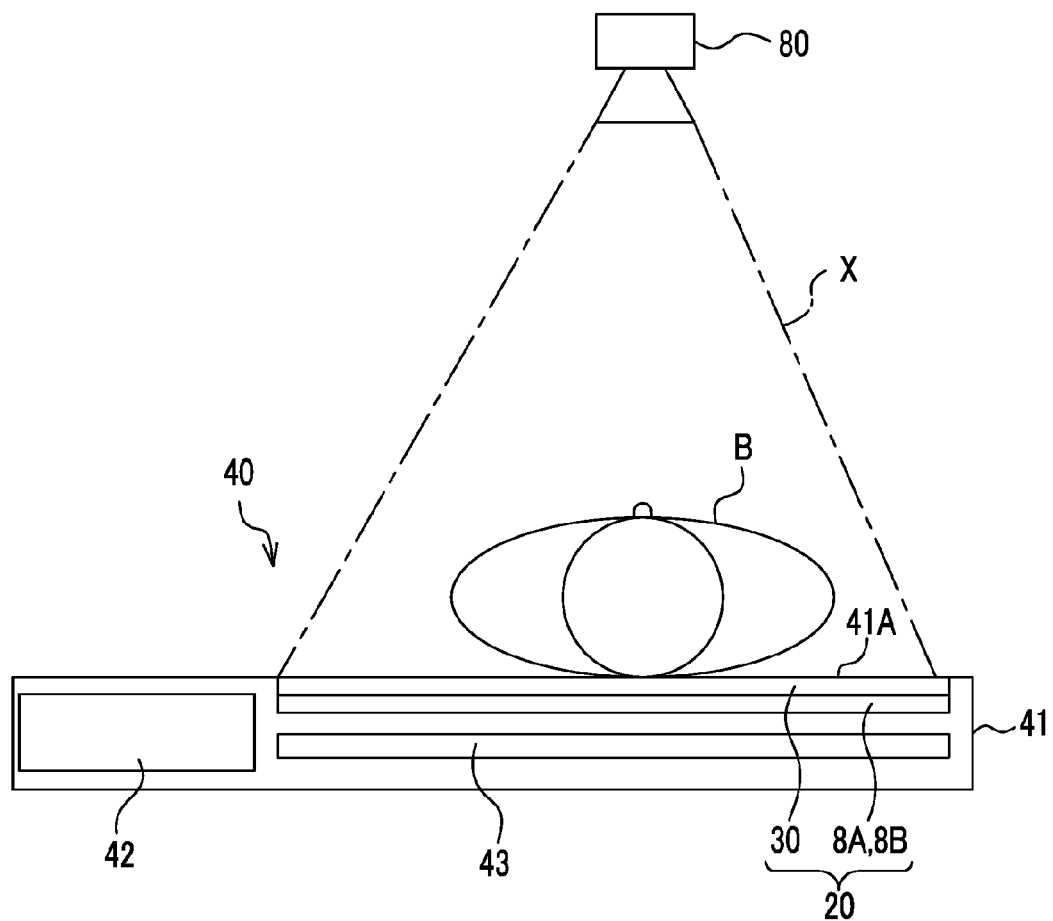
FIG. 7 is a cross-sectional view showing the configuration of the electronic cassette according to the first embodiment.

As shown in FIG. 6, the electronic cassette 40 includes a plate-shaped housing 41 formed of a material which allows a radiation to be transmitted therethrough. Therefore, the electronic cassette 40 has a waterproof and sealing structure. In the housing 41, the radiation detector 20 that detects a radiation X emitted from the irradiation surface side of the housing 41, at which the radiation X is irradiated, and transmitted through a subject and a lead (Pb) plate 43 which absorbs back scattered rays of the radiation X are disposed in this order. In the housing 41, a region corresponding to the arrangement position of the radiation detector 20 on one plate-shaped surface is a quadrilateral radiographing region 41A where a radiation can be detected. As shown in FIG. 7, the radiation detector 20 is disposed such that the TFT substrate 30 is located on the radiographing region 41A side, and is bonded to the inside of the housing 41 which forms the radiographing region 41A.

In addition, at one end side of the inside of the housing 41, a case 42 in which a cassette control unit 58 or a power supply unit 70 is disposed at the position (outside the range of the radiographing region 41A) not overlapping the radiation detector 20.

Figure 8:
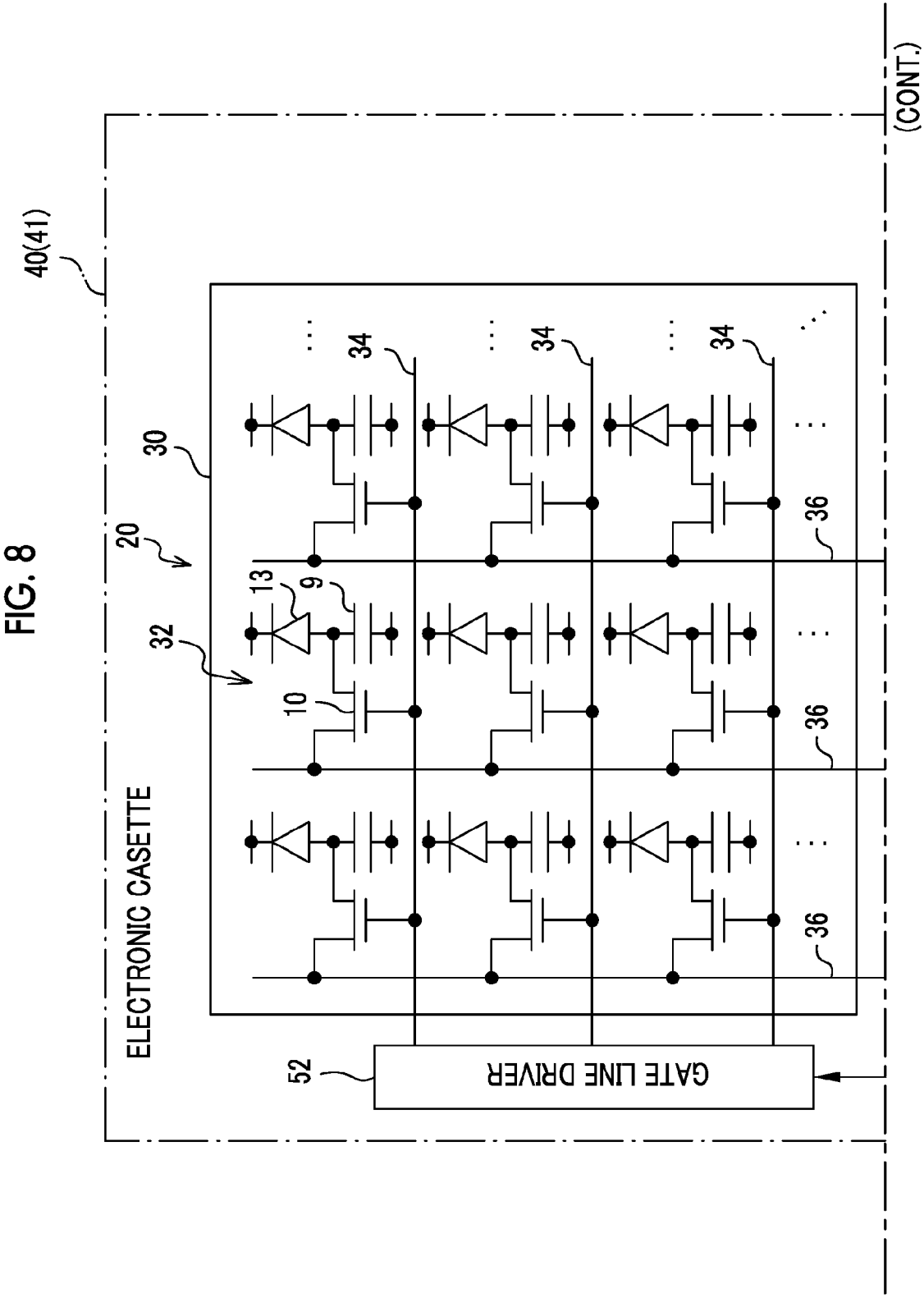
FIG. 8 is a block diagram showing a main part configuration of the electric system of the electronic cassette according to the first embodiment.

FIG. 8 is a block diagram showing a main part configuration of the electric system of the electronic cassette 40 according to the present embodiment.

In the radiation detector 20, a gate line driver 52 is disposed at one of two adjacent sides, and a signal processing unit 54 is disposed at the other side. Each gate wiring line 34 of the TFT substrate 30 is connected to the gate line driver 52, and each data wiring line 36 of the TFT substrate 30 is connected to the signal processing unit 54.

In addition, an image memory 56, the cassette control unit 58, and a radio communication unit 60 are provided inside the housing 41.

Thin film transistors 10 of the TFT substrate 30 are sequentially turned on in units of rows by a signal supplied through the gate wiring line 34 from the gate line driver 52. Electric charges read by the thin film transistor 10 which has been turned on are transmitted through the data wiring line 36 as electric signals and are input to the signal processing unit 54. Thus, electric charges are sequentially read in units of rows. As a result, a two-dimensional radiological image can be acquired.

Although not shown, the signal processing unit 54 has an amplifier circuit, which amplifies an input electric signal, and a sample and hold circuit for each data wiring line 36, and the electric signal transmitted through each data wiring line 36 is amplified by the amplifier and is then held in the sample and hold circuit. In addition, a multiplexer and an A/D (analog to digital) converter are connected to the output side of the sample and hold circuit in order. The electric signal held in each sample and hold circuit is input to the multiplexer in order (serially) and is converted into digital image data by the A/D converter. The generation unit is included in the signal processing unit 54.

The image memory 56 is connected to the signal processing unit 54, and the image data output from the A/D converter of the signal processing unit 54 is stored in the image memory 56 in order. The image memory 56 has a storage capacity capable of storing image data of a predetermined number of sheets. Accordingly, whenever a radiological image is radiographed, image data obtained by the radiographing is sequentially stored in the image memory 56.

The image memory 56 is connected to the cassette control unit 58. The cassette control unit 58 is formed by a microcomputer, and includes a CPU (Central Processing Unit) 58A, a memory 58B including a ROM (Read Only Memory) and a RAM (Random Access Memory), and a nonvolatile storage unit 58C such as a flash memory. The cassette control unit 58 controls the entire operation of the electronic cassette 40.

In addition, the radio communication unit 60 is connected to the cassette control unit 58. The radio communication unit 60 corresponds to the wireless LAN (Local Area Network) standard represented by IEEE (Institute of Electrical and Electronics Engineers) 802.11a/b/g/n or the like, and controls the transmission of various kinds of information to and from an external apparatus through radio communication. Through the radio communication unit 60, the cassette control unit 58 can perform radio communication with an external device such as a console which controls entire radiographing. Accordingly, transmission and reception of various kinds of information between the cassette control unit 58 and the console is possible.

In addition, the power supply unit 70 is provided in the electronic cassette 40, and various circuits or devices described above (microcomputer which functions as the gate line driver 52, the signal processing unit 54, the image memory 56, the radio communication unit 60, or the cassette control unit 58) are operated by electric power supplied from the power supply unit 70. The power supply unit 70 has a built-in battery (secondary battery which can be recharged) so as not to impair the portability of the electronic cassette 40, and electric power is supplied from the charged battery to various circuits or devices. In addition, wiring lines connecting the power supply unit 70 to various circuits or devices are not shown in FIG. 8.

Next, the operation of the electronic cassette 40 according to the present embodiment will be described.

When radiographing a radiological image, the electronic cassette 40 according to the present embodiment is disposed with the radiographing region 41A upward so as to be spaced apart from a radiation generator 80 as shown in FIG. 7, and a radiographed portion B of a patient is placed on the radiographing region. The radiation generator 80 emits the radiation X of a radiation dose according to the radiographing conditions and the like given in advance. The radiation X emitted from the radiation generator 80 is transmitted through the radiographed portion B to carry the image information and is then irradiated to the electronic cassette 40.

The radiation X emitted from the radiation generator 80 reaches the electronic cassette 40 after being transmitted through the radiographed portion B. Electric charges corresponding to the dose of emitted radiation X are generated in each sensor section 13 of the radiation detector 20 built in the electronic cassette 40, and the electric charges generated in the sensor section 13 are accumulated in the capacitor 9.

After the end of emission of the radiation X, the cassette control unit 58 controls the gate line driver to output the ON signal from the gate line driver 52 to each gate wiring line 34 of the radiation detector 20 one line at a time in order, thereby reading the image information. The image information read from the radiation detector 20 is stored in the image memory 56.

Meanwhile, in the electronic cassette 40 according to the present embodiment, as shown in FIG. 7, the radiation detector 20 is provided such that the radiation X is emitted from the TFT substrate 30 side.

Figure 9:
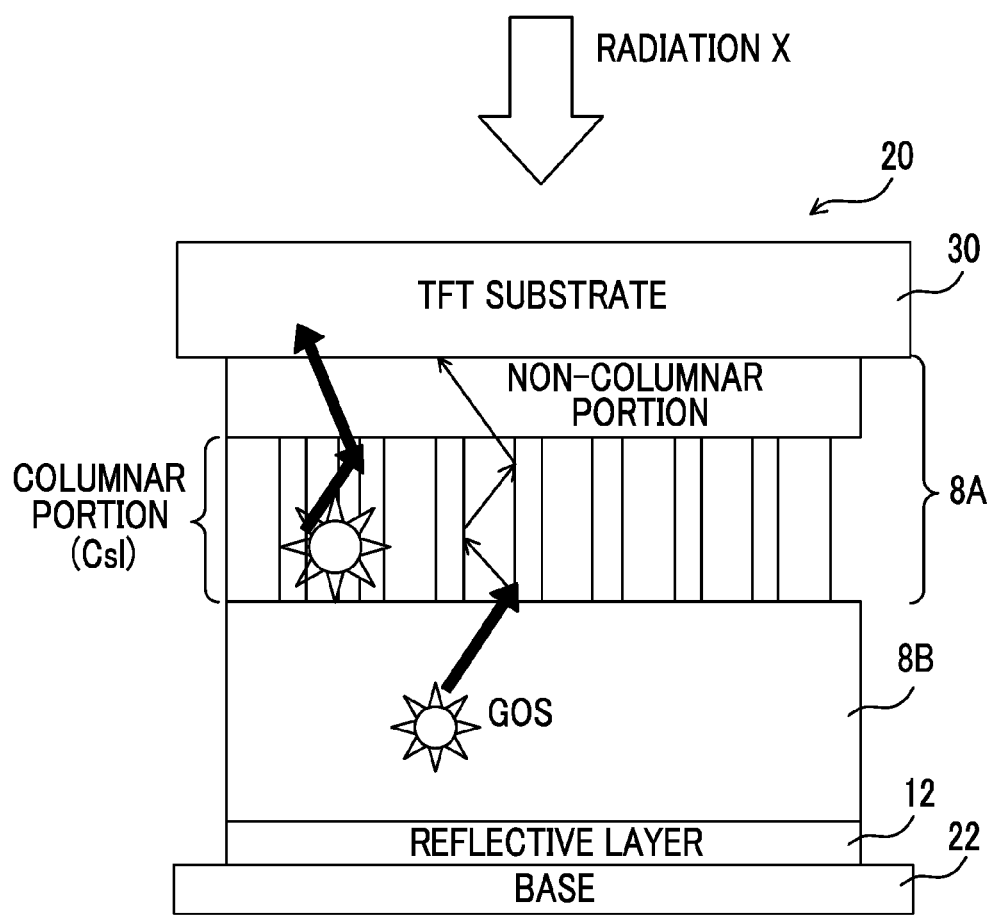
FIG. 9 is a cross-sectional view showing the configuration of the radiation detector according to the first embodiment.

In the radiation detector 20, as shown in FIG. 9, the scintillator 8A configured to include columnar crystals is laminated on the opposite surface of the TFT substrate 30 to the incidence side of the radiation X, and the scintillator 8B is laminated on the opposite surface of the scintillator 8A to the TFT substrate 30 side (incidence side of the radiation X).

For this reason, in the radiation detector 20, the surface of the scintillator 8A laminated on the TFT substrate 30 emits light more strongly than the other surface does. Accordingly, since the light emitting position of the scintillator 8A with respect to the TFT substrate 30 is close compared with a case where the radiation X is emitted from the scintillator 8B side, the resolution of a radiological image obtained by radiographing can be increased. As a result, the quality of the obtained radiological image can be improved.

In addition, in the radiation detector 20, the second light generated by the scintillator 8B is effectively guided to the TFT substrate 30 due to the light guiding function by columnar crystals of the scintillator 8A. Also in this point, the quality of a radiological image can be improved.

In addition, in the radiation detector 20, a radiation which cannot be absorbed by the scintillator 8A can be absorbed by the scintillator 8B. Therefore, the scintillator 8A configured to include relatively high-cost columnar crystals can be made thin. As a result, an increase in cost can be suppressed.

In addition, in the radiation detector 20, since a non-columnar portion is provided in the scintillator 8A, the adhesion between the scintillator 8A and the TFT substrate 30 can be improved. Here, since the non-columnar portion is not essential, a non-columnar portion may not be provided.

In addition, in the radiation detector 20, since the photoelectric conversion layer 4 is formed of an organic photoelectric conversion material, most radiation is not absorbed in the photoelectric conversion layer 4. For this reason, in the radiation detector 20 according to the present embodiment, the radiation X is transmitted through the TFT substrate 30 due to the ISS configuration, but the amount of radiation absorbed by the photoelectric conversion layer 4 is small. Therefore, the deterioration of the sensitivity to the radiation X can be suppressed. In the ISS, the radiation X is transmitted through the TFT substrate 30 and reaches the scintillators 8A and 8B. However, when the photoelectric conversion layer 4 of the TFT substrate 30 is formed of an organic photoelectric conversion material, there is almost no absorption of radiation in the photoelectric conversion layer 4 and accordingly, at least the attenuation of the radiation X can be suppressed. This is suitable for the ISS.

In addition, both the amorphous oxide which forms the active layer 17 of the thin film transistor 10 and the organic photoelectric conversion material which forms the photoelectric conversion layer 4 may be formed as layers at low temperature. For this reason, the substrate 1 can be formed of plastic resin, aramid, or bio-nano fiber with less absorption of radiation. Since the substrate 1 formed in this manner absorbs a small amount of radiation, the deterioration of the sensitivity to the radiation X can be suppressed even if a radiation is transmitted through the TFT substrate 30 by the ISS.

In addition, according to the present embodiment, as shown in FIG. 7, the radiation detector 20 is bonded to a portion equivalent to the photographing region 41A in the housing 41 so that the TFT substrate 30 is located on the photographing region 41A side. However, when the substrate 1 is formed of highly rigid plastic resin, aramid, or bio-nano fiber, the portion equivalent to the photographing region 41A of the housing 4 can be formed to be thin since the rigidity of the radiation detector 20 itself is high. In addition, since the radiation detector 20 itself is flexible when the substrate 1 is formed of highly rigid plastic resin, aramid, or bio-nano fiber, the radiation detector 20 is difficult to damage even if the impact is applied to the photographing region 41A.

In addition, although the case where the transparent insulating layer 7 is provided on the surface of the TFT substrate 30 on which the scintillator 8A is formed has been described in the present embodiment, the present invention is not limited to this, and the scintillator 8A may be directly formed on the top surface of the TFT substrate 30 without providing the transparent insulating layer 7.

Second Embodiment

Next, a second embodiment will be described.

Figure 10:
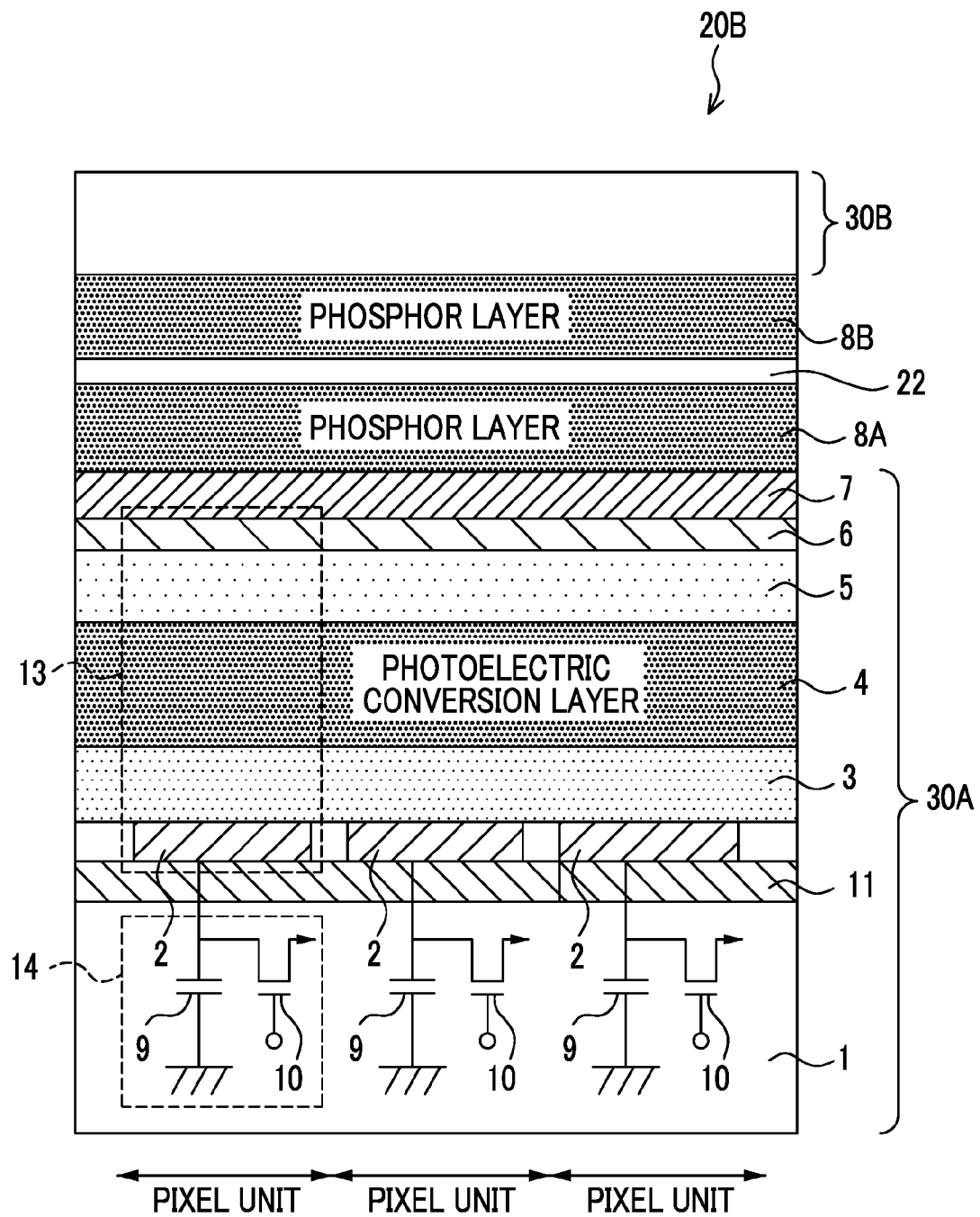
FIG. 10 is a cross-sectional view showing the schematic configuration of three pixel units of a radiation detector according to a second embodiment.

First, the configuration of an indirect conversion type radiation detector 20B according to the second embodiment will be described with reference to FIG. 10.

In the radiation detector 20B, a TFT substrate 30A obtained by forming a signal output section 14, a sensor section 13, and a transparent insulating layer 7 in this order, a scintillator 8A, a scintillator 8B, and a TFT substrate 30B with the same configuration as the TFT substrate 30A are laminated on an insulating substrate 1 in this order. A pixel unit is formed by the signal output sections 14 and the sensor sections 13 of the TFT substrates 30A and 30B. A plurality of pixel units are arrayed on the substrate 1, and each pixel unit is configured such that the signal output section 14 and the sensor section 13 overlap each other. In addition, the TFT substrate 30B is formed by forming the signal output section 14 (second switching element), the sensor section 13 (second photoelectric conversion element), and the transparent insulating layer 7 on the insulating substrate 1 in this order.

In addition, since the scintillators 8A and 8B are the same as those provided in the radiation detector 20 according to the first embodiment, explanation thereof will be omitted herein. In addition, since the configurations of the sensor section 13 and the signal output section 14 are also the same as those of the sensor section 13 and the signal output section 14 of the radiation detector 20 according to the first embodiment, explanation thereof will be omitted herein.

In the meantime, also in the radiation detector 20B according to the present embodiment, the scintillator 8A is directly formed on the TFT substrate 30A by vapor deposition. However, the radiation detector 20B may be manufactured by various methods without being limited to this. Table 2 shows four examples of a method of manufacturing the radiation detector 20B.

TABLE 2

| Manufacturing method | Scintillator 8A | Interface structure | Scintillator 8B |
|---|---|---|---|
| First pattern | Direct vapor deposition | Bonding | Coating + TFT substrate bonding |
| Second pattern | Direct vapor deposition | Pressing + pouch of entire radiation detector | Coating + TFT substrate bonding |
| Third pattern | Indirect vapor deposition + TFT substrate bonding, peeling off of vapor-deposited substrate | Bonding or pressing | Coating + TFT substrate bonding |
| Fourth pattern | Indirect vapor deposition (vapor deposition on scintillator 8B) + TFT substrate bonding | (Unification) | Coating + TFT substrate bonding |

In the manufacturing method of the first pattern, the scintillator 8A is directly formed on the TFT substrate 30A by vapor deposition, and the scintillator 8B is formed by coating on the base 22 formed of polyethylene terephthalate or the like. Then, the surface of the scintillator 8B not facing the base 22 and the TFT substrate 30B are bonded to each other using adhesive or the like. Then, the surface (distal side of columnar crystals) of the scintillator 8A not facing the TFT substrate 30A and the surface of the scintillator 8B not facing the TFT substrate 30B are bonded to each other using adhesive or the like.

In addition, in the manufacturing method of the second pattern, in the same manner as in the first pattern, the scintillator 8A is directly formed on the TFT substrate 30A by vapor deposition, and the scintillator 8B is formed by coating on the base 22 formed of polyethylene terephthalate or the like. Then, the surface of the scintillator 8B not facing the base 22 and the TFT substrate 30B are bonded to each other using adhesive or the like. Then, pouch finishing (lamination) of the entire radiation detector 20B is performed in a state where the surface (distal side of columnar crystals) of the scintillator 8A not facing the TFT substrate 30A and the surface of the scintillator 8B not facing the TFT substrate 30B are pressed against each other.

On the other hand, in the manufacturing method of the third pattern, the scintillator 8A is formed on a vapor-deposited substrate (not shown) by vapor deposition, and the scintillator 8B is formed by coating on the base 22 formed of polyethylene terephthalate or the like in the same manner as in the first and second patterns. Then, the surface of the scintillator 8B not facing the base 22 and the TFT substrate 30B are bonded to each other using adhesive or the like. Then, the surface (distal side of columnar crystals) of the scintillator 8A not facing the vapor-deposited substrate is bonded to the TFT substrate 30A using adhesive or the like so that the vapor-deposited substrate is peeled off from the scintillator 8A, and the surface of the scintillator 8A not facing the TFT substrate 30A and the surface of the scintillator 8B not facing the TFT substrate 30B are bonded to each other using adhesive or the like or are pressed against each other. In the third pattern, a non-columnar portion is formed not on the TFT substrate 30A side but on the scintillator 8B side.

In addition, in the manufacturing method of the fourth pattern, in the same manner as in the first to third patterns, the scintillator 8B is formed by coating on the base 22 formed of polyethylene terephthalate or the like. Then, the surface of the scintillator 8B not facing the base 22 and the TFT substrate 30B are bonded to each other using adhesive or the like. Then, the scintillator 8A is formed on the scintillator 8B by vapor deposition, and the surface (distal side of columnar crystals) of the scintillator 8A not facing the scintillator 8B is bonded to the TFT substrate 30A using adhesive or the like. Also in the fourth pattern, a non-columnar portion is formed not on the TFT substrate 30A side but on the scintillator 8B side.

In addition, also in the radiation detector 20B according to the present embodiment, it is preferable to perform control such that the distal end of each columnar portion of the scintillator 8A is as flat as possible. Here, "flat" means that the distal end of each columnar portion of the scintillator 8A is parallel or approximately parallel to the TFT substrate on which each columnar portion is formed. Specifically, this can be realized by controlling the temperature of the vapor-deposited substrate at the end of vapor deposition. For example, when the temperature of the vapor-deposited substrate at the end of vapor deposition is set to 110°, the angle of the distal end is approximately 170°. When the temperature of the vapor-deposited substrate at the end of vapor deposition is set to 140°, the angle of the distal end is approximately 60°. When the temperature of the vapor-deposited substrate at the end of vapor deposition is set to 200°, the angle of the distal end is approximately 70°. When the temperature of the vapor-deposited substrate at the end of vapor deposition is set to 260°, the angle of the distal end is approximately 120°. In addition, this control is disclosed in detail in JP2010-25620A. Accordingly, explanation thereof will be omitted.

In addition, in the first to fourth patterns described above, the base 22 is left on the surface of the scintillator 8B not facing the TFT substrate 30B. However, the base 22 may be peeled off before the scintillators 8A and 8B are bonded to each other.

In addition, similar to the TFT substrate 30 according to the first embodiment shown in FIG. 5, a plurality of pixels 32 each of which is configured to include the sensor section 13, the capacitor 9, and the thin film transistor 10 are provided on the TFT substrates 30A and 30B in a two-dimensional manner in a fixed direction (row direction) and a direction (column direction) crossing the fixed direction.

In addition, corresponding to each of the TFT substrates 30A and 30B, a plurality of gate wiring lines 34 which extend in the above-described fixed direction (row direction) and serve to turn each thin film transistor 10 on and off and a plurality of data wiring lines 36 which extend in the above-described crossing direction (column direction) and serve to read electric charges through the thin film transistor 10 in the ON state are provided in the radiation detector 20B.

Next, the configuration of the electronic cassette 40 in which such a radiation detector 20B is provided will be described.

Figure 11:
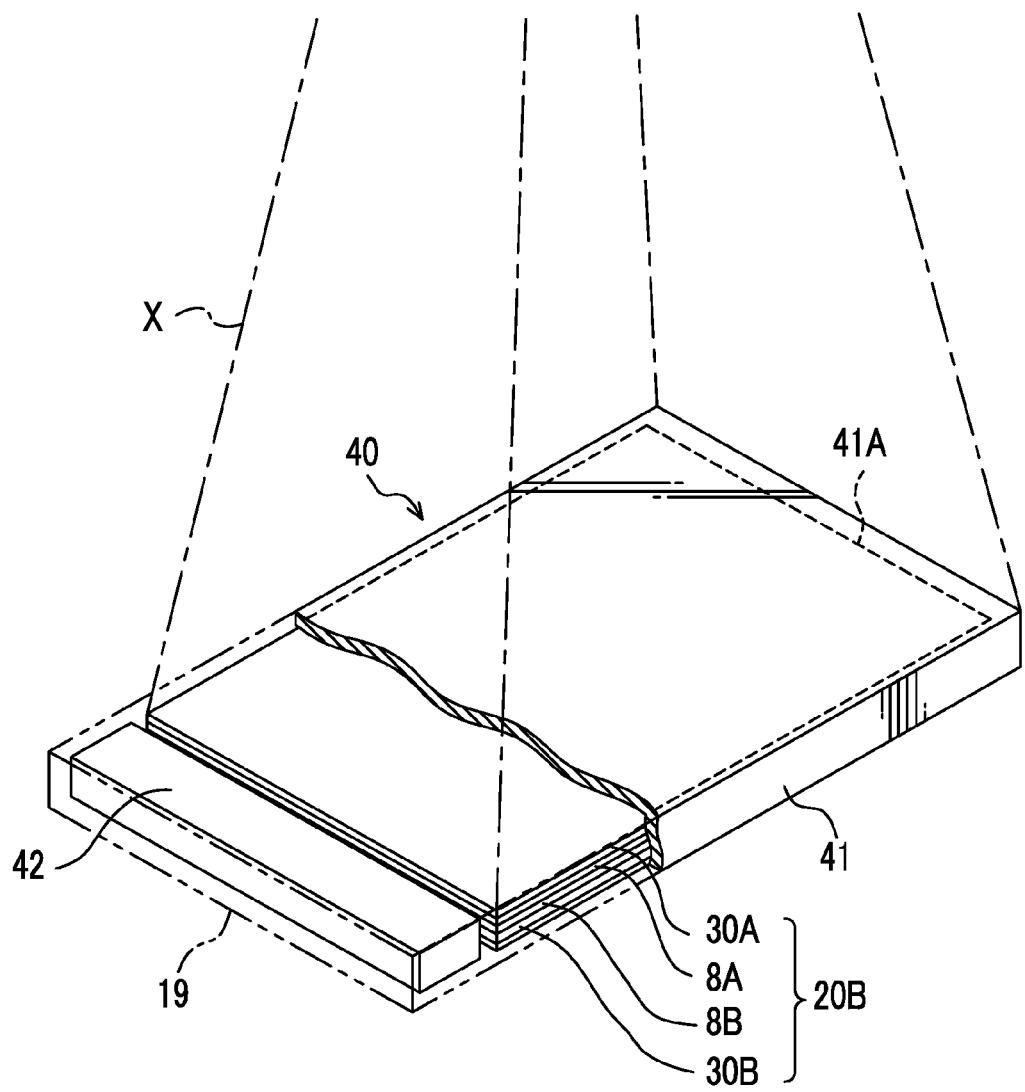
FIG. 11 is a perspective view showing the configuration of an electronic cassette according to the second embodiment.
Figure 12:
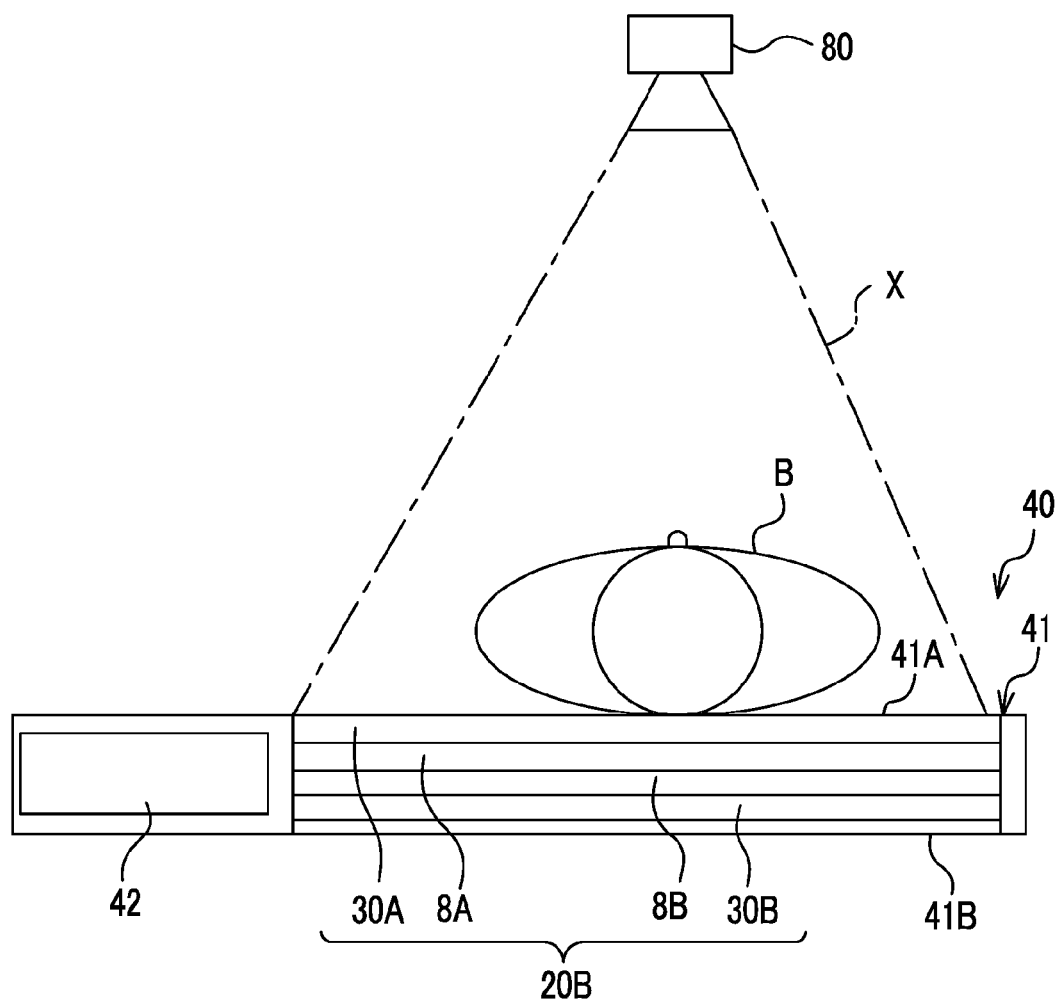
FIG. 12 is a cross-sectional view showing the configuration of the electronic cassette according to the second embodiment.

FIG. 11 is a perspective view showing the configuration of the electronic cassette 40 according to the present embodiment, and FIG. 12 is a cross-sectional view of the electronic cassette 40.

In the electronic cassette 40, the radiation detector 20B is disposed inside a housing 41. In the housing 41, a region corresponding to the arrangement position of the radiation detector 20B on one plate-shaped surface is a radiographing region 41A to which a radiation is emitted at the time of radiographing.

Figure 13:
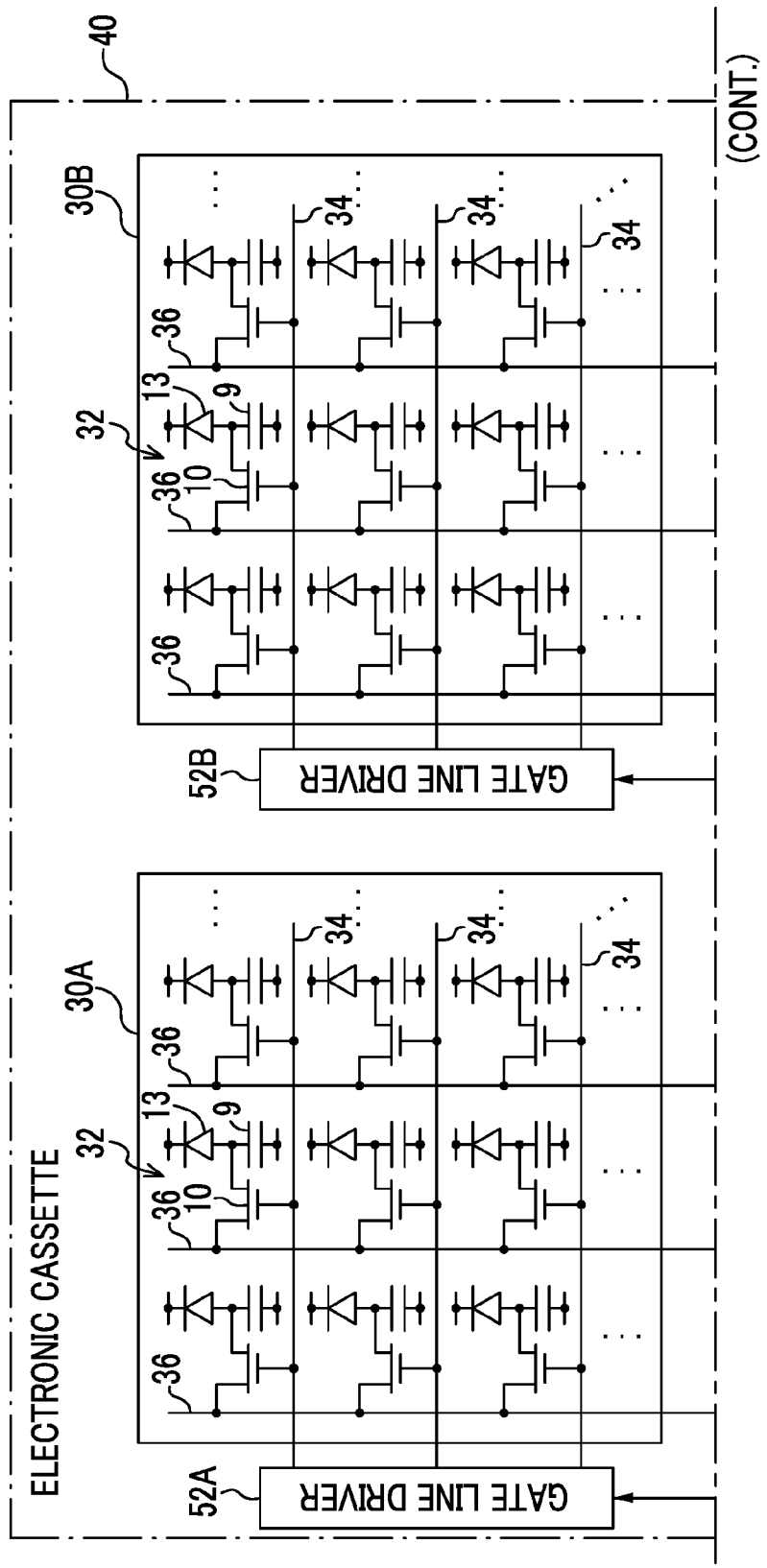
FIG. 13 is a block diagram showing a main part configuration of the electric system of the electronic cassette according to the second embodiment.

FIG. 13 is a block diagram showing a main part configuration of the electric system of the electronic cassette 40 according to the present embodiment.

In each of the TFT substrates 30A and 30B, a gate line driver 52 is disposed at one of two adjacent sides, and a signal processing unit 54 is disposed at the other side. Hereinafter, when the gate line driver 52 and the signal processing unit 54 provided corresponding to the two TFT substrates 30A and 30B need to be distinguished from each other, reference numeral A is given to the gate line driver 52 and the signal processing unit 54 corresponding to the TFT substrate 30A and reference numeral B is given to the gate line driver 52 and the signal processing unit 54 corresponding to the TFT substrate 30B in the following explanation.

Each gate wiring line 34 of the TFT substrate 30A is connected to the gate line driver 52A, and each data wiring line 36 of the TFT substrate 30A is connected to the signal processing unit 54A. Each gate wiring line 34 of the TFT substrate 30B is connected to the gate line driver 52B, and each data wiring line 36 of the TFT substrate 30B is connected to the signal processing unit 54B.

Thin film transistors 10 of each of the TFT substrates 30A and 30B are sequentially turned on in units of rows by a signal supplied through the gate wiring line 34 from each of the gate line drivers 52A and 52B. Electric charges read by the thin film transistor 10 which has been turned on are transmitted through the data wiring line 36 as electric signals and are input to the signal processing units 54A and 54B. Thus, electric charges are sequentially read in units of rows. As a result, a two-dimensional radiological image can be acquired.

The image memory 56 is connected to the signal processing units 54A and 54B, and the image data output from the A/D converters of the signal processing units 54A and 54B is stored in the image memory 56 in order.

Since the cassette control unit 58 controls the operations of the gate line drivers 52A and 52B separately, the reading of image information indicating a radiological image from the TFT substrates 30A and 30B can be separately controlled.

Next, the operation of the electronic cassette 40 according to the present embodiment will be described.

When radiographing a radiological image, the electronic cassette 40 according to the present embodiment is disposed with the radiographing region 41A upward so as to be spaced apart from a radiation generator 80 as shown in FIG. 12, and a radiographed portion B of a patient is placed in the radiographing region. The radiation generator 80 emits the radiation X of a radiation dose according to the radiographing conditions and the like given in advance. The radiation X emitted from the radiation generator 80 is transmitted through the radiographed portion B to carry the image information and is then irradiated to the electronic cassette 40.

The radiation X emitted from the radiation generator 80 reaches the electronic cassette 40 after being transmitted through the radiographed portion B. Electric charges corresponding to the dose of emitted radiation X are generated in each sensor section 13 of the radiation detector 20B built in the electronic cassette 40, and the electric charges generated in the sensor section 13 are accumulated in the capacitor 9.

After the end of emission of the radiation X, the cassette control unit 58 controls the gate line drivers 52A and 52B to output the ON signal from the gate line drivers 52A and 52B to each gate wiring line 34 of the TFT substrates 30A and 30B one line at a time in order, thereby reading the image information. The image information read from the radiation detector 20B is stored in the image memory 56. In addition, in the electronic cassette 40 according to the present embodiment, image information read from the TFT substrate 30A (hereinafter, referred to as "first image information") and image information read from the TFT substrate 30B (hereinafter, referred to as "second image information") are stored in different storage regions of the image memory 56.

Meanwhile, in the electronic cassette 40 according to the present embodiment, operation mode instruction information indicating which operation mode is to be applied between an operation mode (hereinafter, referred to as an "additive radiographing mode"), in which the first image information and the second image information are transmitted from an external device such as a console that performs overall control of the radiation generator 80 and the electronic cassette 40 after being added for each corresponding pixel, and an operation mode (hereinafter, referred to as a "normal radiographing mode"), in which only the first image information is transmitted without performing the addition, is received through the radio communication unit 60. In addition, after the end of emission of the radiation X, the cassette control unit 58 executes image information transmission processing for transmitting the image information according to the operation mode indicated by the operation mode instruction information received in advance.

Hereinafter, the operation of the electronic cassette 40 when executing the image information transmission processing will be described with reference to FIG. 14. In addition, FIG. 14 is a flow chart showing the process flow of an image information transmission processing program executed by the CPU 58A in the cassette control unit 58 of the electronic cassette 40 in this case, and the program is stored in the memory 58B in advance.

In step 100 in FIG. 9, it is determined whether or not the operation mode indicated by the received operation mode instruction information is the additive radiographing mode. If positive determination is made, the process proceeds to step 102 and waits until both the first image information and the second image information are stored in the image memory 56.

In next step 104, the second image information is added to the first image information stored in the image memory 56 for each corresponding pixel. Then, the process proceeds to step 108.

On the other hand, when negative determination is made in step 100, the operation mode indicated by the received operation mode instruction information is regarded as a normal radiographing mode, and the process proceeds to step 106 and waits until the first image information is stored in the image memory 56. Then, the process proceeds to step 108.

In step 108, the first image information is transmitted to the external device through the radio communication unit 60. Then, this image information transmission processing program ends.

Meanwhile, in the electronic cassette 40 according to the present embodiment, as shown in FIG. 12, the radiation detector 20B is provided such that the radiation X is emitted from the TFT substrate 30A side.

Figure 15:
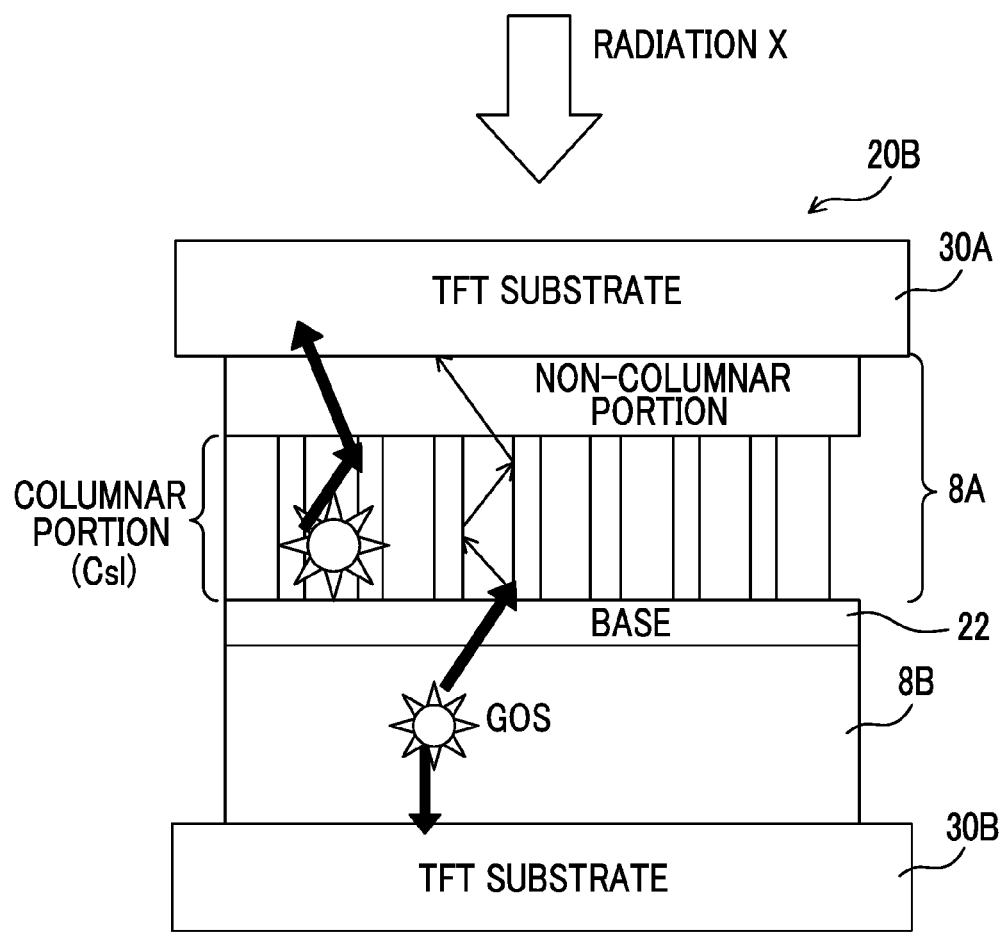
FIG. 15 is a cross-sectional view showing the configuration of the radiation detector according to the second embodiment.

In the radiation detector 20B, as shown in FIG. 15, the scintillator 8A configured to include columnar crystals is laminated on the opposite surface of the TFT substrate 30A to the incidence side of the radiation X, and the scintillator 8B is laminated on the opposite surface of the scintillator 8A to the TFT substrate 30A side (incidence side of the radiation X).

For this reason, in the radiation detector 20B, the surface of the scintillator 8A laminated on the TFT substrate 30A emits light more strongly than the other surface does. Accordingly, since the light emitting position of the scintillator 8A with respect to the TFT substrate 30A is close compared with a case where the radiation X is emitted from the scintillator 8B side, the resolution of a radiological image obtained by radiographing can be increased. As a result, the quality of the obtained radiological image can be improved.

In addition, in the radiation detector 20B, the second light generated by the scintillator 8B is effectively guided to the TFT substrate 30A due to the light guiding function by columnar crystals of the scintillator 8A. Also in this point, the quality of a radiological image can be improved.

In addition, in the radiation detector 20B, a radiation which cannot be absorbed by the scintillator 8A can be absorbed by the scintillator 8B. Therefore, the scintillator 8A configured to include relatively high-cost columnar crystals can be made thin. As a result, an increase in cost can be suppressed.

Moreover, in the radiation detector 20B, a part of the second light generated by the scintillator 8B is received in the TFT substrate 30B and accordingly image information obtained by the TFT substrate 30B can be used. By using the result obtained by addition of this image information and image information obtained by the TFT substrate 30A for each corresponding pixel, the sensitivity of the entire radiation detector 20B can be improved. As a result, since the dose of radiation X emitted from the radiation generator 80 when radiographing a radiological image can be reduced, the amount of exposure to a patient can be reduced.

For this reason, such a form of using a result obtained by adding the image information is particularly useful in moving image radiographing. In addition, in this form, the image information obtained by the scintillator 8B is obtained by the PSS method. Therefore, the radiological image obtained by the above-described addition does not necessarily have high quality, but sufficient quality to radiograph a moving image can be obtained. When high quality is required in radiographing a still image, it is also possible to use only the first image information without performing the above-described addition.

In addition, in the radiation detector 20, since a non-columnar portion is provided in the scintillator 8A, the adhesion between the scintillator 8A and the TFT substrate 30A can be improved. Here, by bringing the porosity of the non-columnar portion close to 0 (zero), reflection of light by the non-columnar portion can be preferably suppressed. In addition, it is preferable that the non-columnar portion be made as thin as possible (approximately 10 μm).

Thus, in the radiation detector 20B according to the present embodiment, the non-columnar portion is provided in the scintillator 8A. However, the non-columnar portion may not be provided without being limited to this. In addition, in FIG. 15, a half mirror (not shown) may be provided between the base 22 and the scintillator 8A so that light from the scintillator 8A is reflected from the half mirror and is then received by the TFT substrate 30A and light from the scintillator 8B is transmitted through the half mirror and is then received by the TFT substrate 30A. Thus, since the light generated by the scintillator 8A is efficiently received by the TFT substrate 30A through the scintillator 8A, the quality of the obtained radiological image can be improved.

In addition, in the radiation detector 20B, since the photoelectric conversion layer 4 is formed of an organic photoelectric conversion material, most radiation is not absorbed in the photoelectric conversion layer 4. For this reason, in the radiation detector 20B according to the present embodiment, the radiation X is transmitted through the TFT substrate 30A due to the ISS configuration, but the amount of radiation absorbed by the photoelectric conversion layer 4 is small. Therefore, the deterioration of the sensitivity to the radiation X can be suppressed. In the ISS, the radiation X is transmitted through the TFT substrate 30A and reaches the scintillators 8A and 8B. However, when the photoelectric conversion layer 4 of the TFT substrate 30A is formed of an organic photoelectric conversion material, there is almost no absorption of radiation in the photoelectric conversion layer 4 and accordingly, at least the attenuation of the radiation X can be suppressed. This is suitable for the ISS.

In addition, both the amorphous oxide which forms the active layer 17 of the thin film transistor 10 and the organic photoelectric conversion material which forms the photoelectric conversion layer 4 may be formed as layers at low temperature. For this reason, the substrate 1 can be formed of plastic resin, aramid, or bio-nano fiber with less absorption of radiation. Since the substrate 1 formed in this manner absorbs a small amount of radiation, the deterioration of the sensitivity to the radiation X can be suppressed even if a radiation is transmitted through the TFT substrate 30A by the ISS.

In addition, according to the present embodiment, as shown in FIG. 12, the radiation detector 20B is bonded to a portion equivalent to the photographing region 41A in the housing 41 so that the TFT substrate 30A is located on the photographing region 41A side. However, when the substrate 1 is formed of highly rigid plastic resin, aramid, or bio-nano fiber, the portion equivalent to the photographing region 41A of the housing 4 can be formed to be thin since the rigidity of the radiation detector 20B itself is high. In addition, since the radiation detector 20B itself is flexible when the substrate 1 is formed of highly rigid plastic resin, aramid, or bio-nano fiber, the radiation detector 20B is difficult to damage even if the impact is applied to the photographing region 41A.

In addition, although the case where the transparent insulating layer 7 is provided on the surface of the TFT substrate 30A on which the scintillator 8A is formed has been described in the present embodiment, the present invention is not limited to this, and the scintillator 8A may be directly formed on the top surface of the TFT substrate 30A without providing the transparent insulating layer 7.

While the present invention has been described using the embodiments, the technical scope of the present invention is not limited to the scope described in each embodiment described above. Various changes or modifications may be made in the above embodiments without departing from the spirit and scope of the present invention, and forms in which such changes or modifications are added are also included in the technical scope of the invention.

In addition, the above-described embodiments do not limit the invention defined in the appended claims, and all combinations of the features described in the embodiments are not necessary for the solving means of the invention. Inventions of various stages are included in each of the embodiments described above, and various inventions may be extracted by proper combination of a plurality of components disclosed. Even if some components are removed from all components shown in the embodiments, the configuration where some components are removed may also be extracted as an invention as long as the effect of the present invention is obtained.

For example, in each of the embodiments, the case has been described in which the present invention is applied to the electronic cassette 40 which is a portable radiological image radiographing apparatus. However, the present invention is not limited to this, and may also be applied to a stationary radiological image radiographing apparatus.

In addition, in each of the embodiments, the case has been described in which a layer including CsI is applied as the first phosphor layer of the present invention. However, the present invention is not limited to this, and other layers including columnar crystals, such as CsBr, can be applied.

In addition, in each of the embodiments, the case has been described in which a layer including GOS is applied as the second phosphor layer of the present invention. However, the present invention is not limited to this, and other phosphors such as BaFBr with different energy characteristics of absorbed radiations from the first phosphor layer can be applied.

In addition, although the case where the cassette control unit 58 or the power supply unit 70 is disposed inside the housing 41 of the electronic cassette 40 so as not to overlap the case 42 and the radiation detector has been described in each of the embodiments, the present invention is not limited to this. For example, the radiation detector and the cassette control unit 58 or the power supply unit 70 may be disposed so as to overlap each other.

In addition, although the case where the TFT substrate 30B is provided on the opposite surface of the scintillator 8B to the radiation incidence side has been described, the present invention is not limited to this. For example, as shown in FIG. 16, the TFT substrate 30B may also be provided on the radiation incidence side surface of the scintillator 8B.

Figure 16:
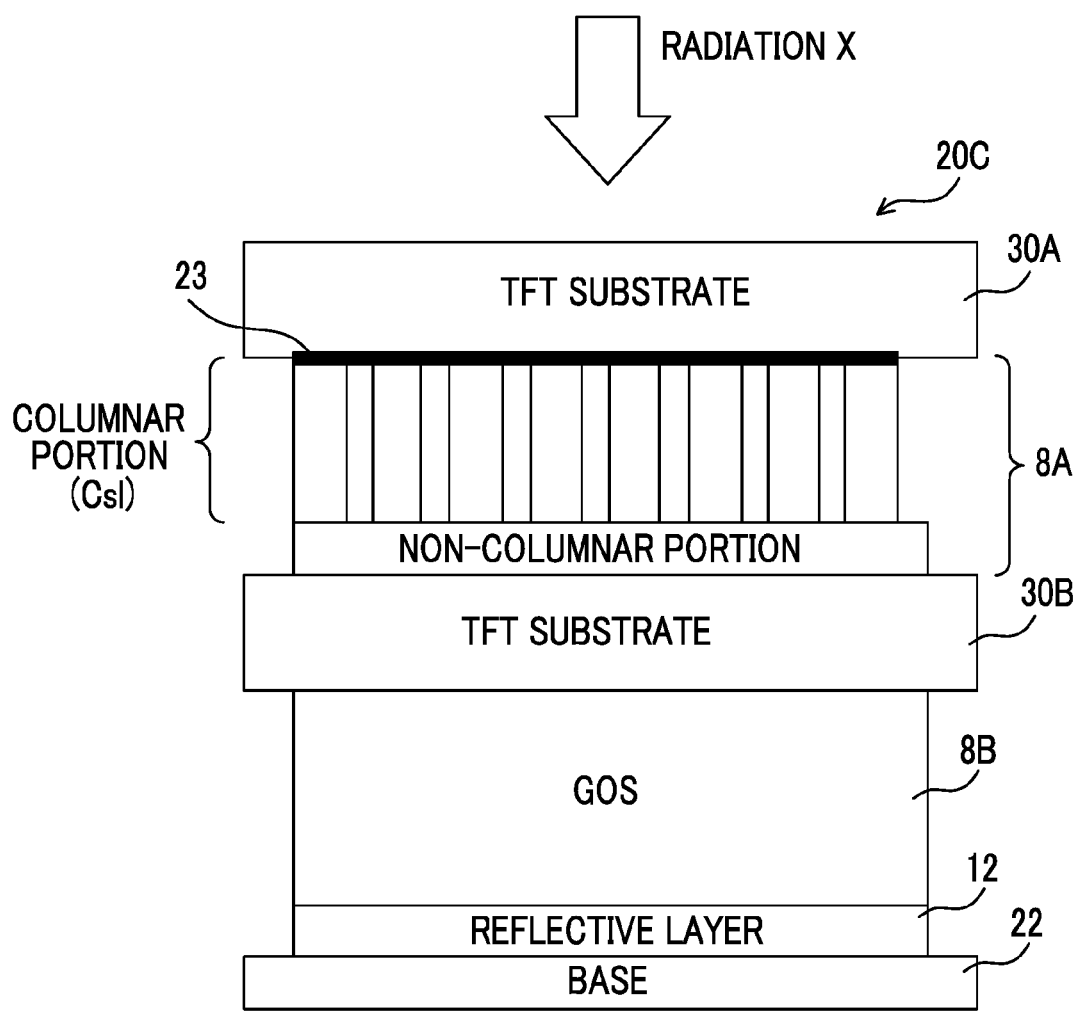
FIG. 16 is a cross-sectional view showing the configuration of a radiation detector according to another embodiment.

Here, in a radiation detector 20C shown in FIG. 16, a TFT substrate 30A, an adhesion layer 23, a scintillator 8A, a TFT substrate 30B, a scintillator 8B, a reflective layer 12, and a base 22 are laminated in this order. In addition, in this radiation detector 20C, the distal ends of columnar crystals in the scintillator 8A are located on the TFT substrate 30A side. Therefore, the quality of a radiological image obtained as a result can be improved.

In addition, in this form, the distal ends of the columnar crystals of the scintillator 8A are laminated on the TFT substrate 30A after forming the scintillator 8A on a vapor-deposited substrate (not shown), and then the vapor-deposited substrate is peeled off. However, if light emitted from the scintillator 8A is not received by the TFT substrate 30B, the process of peeling off the vapor-deposited substrate is not necessary. In addition, if a light-transmissive and heat-resistant resin substrate is used as the vapor-deposited substrate, the process of peeling off the vapor-deposited substrate is not necessary either.

In addition, in the radiation detector 20C, it is preferable that both the TFT substrates 30A and 30B be flexible substrates. In this case, even if the positions of the distal ends of columnar crystals of the scintillator 8A are not aligned, the adhesion between the scintillator 8A and the TFT substrate 30A and between the scintillator 8A and the TFT substrate 30B can be improved. Moreover, in this case, as a flexible substrate applied, it is preferable to apply a substrate, which uses ultra-thin glass based on the floating method developed in recent years as a base, in order to improve the transmittance of radiation. In addition, ultra-thin glass applicable in this case is disclosed in "Success in the development of ultra-thin glass with a thickness of 0.1 mm (thinnest in the world) using the floating method, Asahi Glass Co., Ltd., [online],

[Searched on Aug. 20, 2011], the Internet <URL:http://www.agc.com/news/2011/0516.pdf>", for example.

Figure 17:
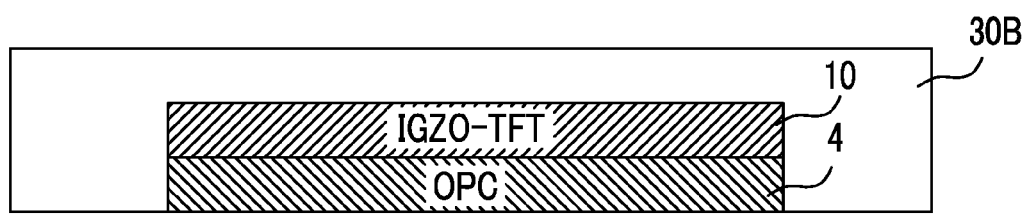
FIG. 17 is a cross-sectional view showing the configuration of a radiation detector according to another embodiment.
Figure 18:
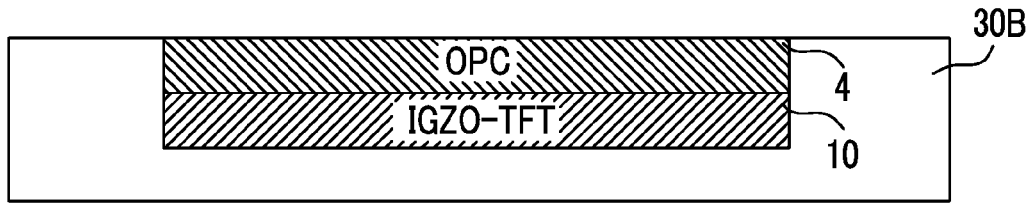
FIG. 18 is a cross-sectional view showing the configuration of a radiation detector according to another embodiment.

Moreover, in the radiation detector 20C, when the photoelectric conversion layer 4 of the sensor section 13 of the TFT substrate 30B is formed of an organic photoelectric conversion material and the active layer 17 of the thin film transistor 10 is formed of IGZO, the photoelectric conversion layer 4 may be located on the scintillator 8B side with respect to the thin film transistor 10 as schematically shown in FIG. 17, or the photoelectric conversion layer 4 may be located on the scintillator 8A side with respect to the thin film transistor 10 as schematically shown in FIG. 18. In addition, when the photoelectric conversion layer 4 is located on the scintillator 8B side with respect to the thin film transistor 10, the sensitivity range of IGZO is 460 nm or less. Accordingly, since the photoelectric conversion layer 4 does not have sensitivity in the emission wavelength by GOS, emission by GOS does not become switching noise, which is preferable.

In addition, as the sensor section 13 of each of the radiation detectors 20, 20B, and 20C, an organic CMOS sensor can be used in which the photoelectric conversion layer 4 is formed of a material including an organic photoelectric conversion material. Moreover, as the TFT substrates 30, 30A, and 30B of the radiation detectors 20, 20B, and 20C, an organic TFT array sheet obtained by arraying an organic transistor including an organic material as the thin film transistor 10 on a flexible sheet in an array form can be used. The above organic CMOS sensor is disclosed in JP2009-212377A, for example. In addition, the above organic TFT array sheet is disclosed in The University of Tokyo has developed the ultra-flexible organic transistor, Nihon Keizai Shimbun, [online], [Searched on May 8, 2011], the Internet <URL:http://www.nikkei.com/tech/trend/article/
g=96958A9C93819499E2EAE2E0E48DE2E
AE3E3E0E2E3E2E2E2E2E2E2E2;
p=9694E0E7E2E6E0E2E3E2E2E0E2E0>", for example.

When a CMOS sensor is used as the sensor section 13 of each radiation detector, there is an advantage in that photoelectric conversion can be performed at high speed. In addition, since the substrate can be formed to be thin, there is an advantage in that the absorption of a radiation when the ISS method is adopted can be suppressed and the CMOS sensor can also be appropriately applied to photographing by mammography.

In contrast, as a defect when the CMOS sensor is used as the sensor section 13 of each radiation detector, low resistance to radiation when a crystalline silicon substrate is used may be mentioned. For this reason, there is also a known technique, such as providing an FOP (fiber optic plate) between the sensor section and the TFT substrate, for example.

In consideration of this defect, a SiC (silicon carbide) substrate may be applied as a semiconductor substrate with high resistance to radiation. By using the SiC substrate, there is an advantage in that the ISS method can be used. In addition, since SiC has low internal resistance and the small amount of heat generation compared with Si, there are advantages in that the amount of heat generation when performing moving image radiographing can be suppressed and a sensitivity reduction according to an increase in the temperature of CsI can be suppressed.

Figure 19:
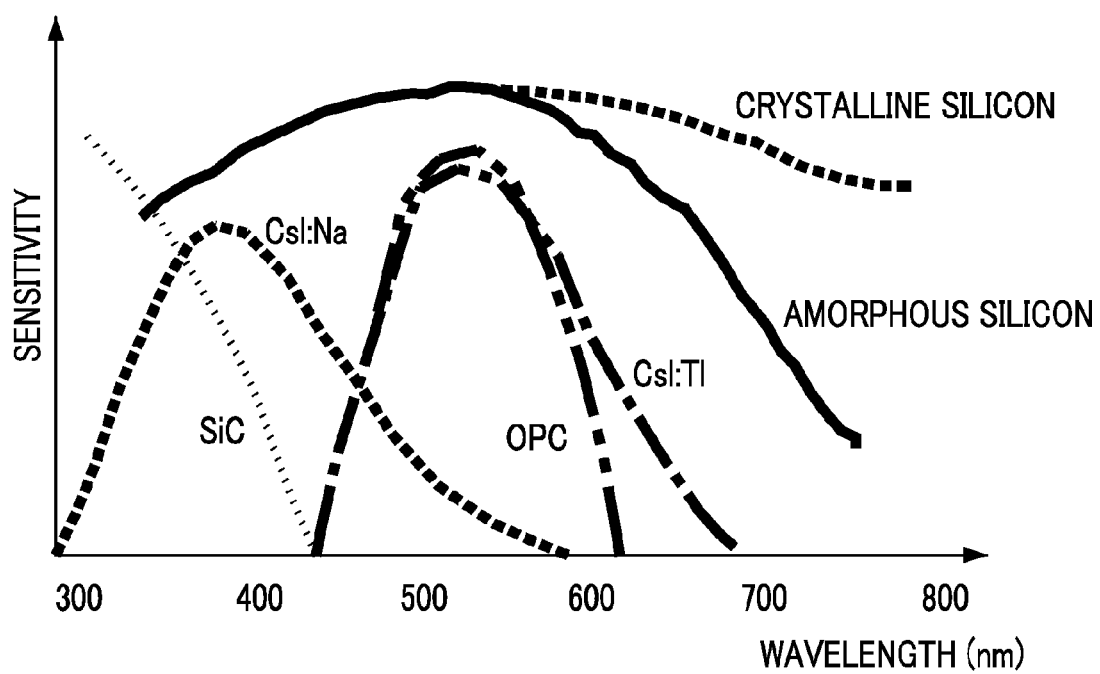
FIG. 19 is a graph showing an example of the sensitivity characteristics of various materials.

Thus, a substrate with high resistance to radiation, such as a SiC substrate, has generally a wide cap (up to approximately 3 eV). As an example, as shown in FIG. 19, an absorption edge is approximately 440 nm corresponding to the blue region. In this case, therefore, it is not possible to use scintillators, such as CsI:Tl or GOS, which emits light in the green region. In addition, FIG. 19 shows spectra of various materials when quinacridone is used as an organic photoelectric conversion material.

On the other hand, since a scintillator that emits light in the green region has actively been studied from the sensitivity characteristics of amorphous silicon, there is a high demand for using the scintillator. For this reason, by forming the photoelectric conversion layer 4 using a material including an organic photoelectric conversion material which absorbs light emitted in the green region, the scintillator which emits light in the green region may be used.

When the photoelectric conversion layer 4 is formed of a material including an organic photoelectric conversion material and the thin film transistor 10 is formed using the SiC substrate, sensitivity wavelength regions of the photoelectric conversion layer 4 and the thin film transistor 10 are different. Therefore, light emitted by the scintillator does not become noise of the thin film transistor 10.

In addition, when SiC and the material including the organic photoelectric conversion material are laminated as the photoelectric conversion layer 4, light emitted mainly in the blue region, such as CsI:Na, may be received and light emitted in the green region may also be received, resulting in the improvement in sensitivity. In addition, since the organic photoelectric conversion material absorbs almost no radiation, the organic photoelectric conversion material can be appropriately used for the ISS method.

In addition, the reason why SiC has high resistance to radiation is that an atomic nucleus is not easily flipped even if struck by the radiation. This point is disclosed in "Development of a semiconductor device which can be used for a long time under high radiation environment such as the space or nuclear field, the Institute of Atomic Energy Research of Japan, [online], [Searched on May 8, 2011], the Internet <URL:http://www.jaea.go.jp/jari/jpn/publish/01/ff/ff36/sic.html>", for example.

In addition, as semiconductor materials with high resistance to radiation other than SiC, C (diamond), BN, GaN, AlN, ZnO, and the like may be mentioned. The reason why these light-element semiconductor materials have high resistance to radiation is that these are mainly wide-gap semiconductors and therefore, the reaction cross-sectional area is small since high energy is required for ionization (electron-hole pair formation) and atomic displacement does not occur easily since bonding between atoms is strong. In addition, this point is disclosed in "New development of nuclear electronics, the Institute of Advanced Electronic Research of Japan, [online], [Searched on May 8, 2011], the Internet <URL:http://www.aist.go.jp/ETL/jp/results/bulletin/pdf/62-10to11/kobayashi150.pdf> or "Studies on radiation-proof characteristics of zinc oxide based electronic devices, Wakasa Wan Energy Research Center, 2009 (fiscal year), public joint research report, March, 2010", for example. In addition, the radiation-proof characteristics of GaN are disclosed in "Evaluation of radiation resistance of gallium nitride elements, University of Tohoku, [online], [Searched on May 8, 2011], the Internet <URL:http://cycgwl.cyric.tohoku.ac.jp/~sakemi/ws2007/ws/pdf/narita.pdf>", for example.

In addition, as applications of GaN other than the blue LED, IC formation in the field of power systems has been studied since GaN has a good thermal conductivity and high insulation resistance. In addition, ZnO has been studied as an LED which emits light mainly in the blue to ultraviolet region.

Meanwhile, in the case of using SiC, a band gap Eg is approximately 1.1 to 2.8 eV of Si. Accordingly, the absorption wavelength $\lambda$ of light shifts to the short wavelength side.

Figure 20:
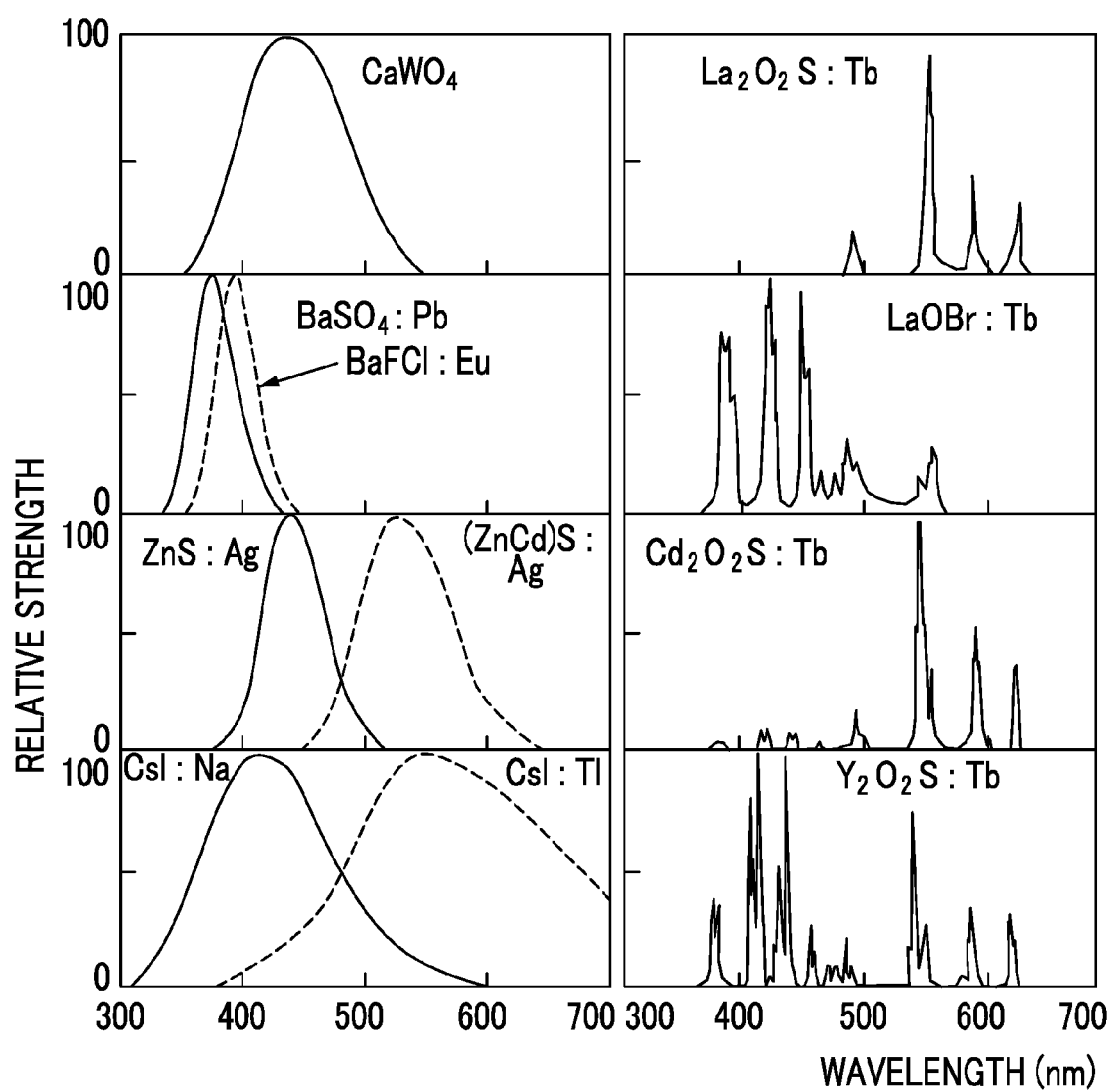
FIG. 20 is a graph showing an example of the sensitivity characteristics of various materials.

Specifically, since the wavelength λ is 1.24/Eg×1000, the sensitivity changes at the wavelength up to approximately 440 nm. Therefore, in the case of using SiC, as shown in FIG. 20 as an example, CsI:Na (peak wavelength: approximately 420 nm) which emits light in the blue region is appropriate as the emission wavelength of the scintillator rather than CsI:Tl (peak wavelength: approximately 565 nm) which emits light in the green region. Since a phosphor preferably emits blue light, CsI:Na (peak wavelength: approximately 420 nm), BaFX:Eu (X is halogen such as Br or I, peak wavelength: approximately 380 nm), $CaWO_4$ (peak wavelength: approximately 425 nm), ZnS:Ag (peak wavelength: approximately 450 nm), LaOBr:Tb, $Y_2O_2S$:Tb, and the like are suitable as phosphors. In particular, CsI:Na, BaFX:Eu used in the CR cassette or the like, and $CaWO_4$ used in a screen, a film, or the like are preferably used.

On the other hand, a CMOS sensor with high resistance to radiation may be formed by using a structure of "Si substrate/thick film $SiO_2$/organic photoelectric conversion material" based on Silicon On Insulator (SOI).

As technology applicable to this configuration, for example, "Building the world's first basis for the development of high-performance logic integrated circuit with radiation-proof characteristics by combination of commercial state-of-the-art SOI technology and radiation-proof technology for space application, Space Science Laboratory, the Japan Aerospace Exploration Agency (JAXA), [online], [Searched on May 8, 2011], the Internet <URL:http://www.jaxa.jp/press/2010/11/20101122_soi_j.html>" may be mentioned.

In addition, since the radiation resistance of the thick-film $SiO_2$ is high in the SOI, complete separation type thick-film SiO, a partial separation type thick-film SiO, and the like may be exemplified as high radiation durable elements. In addition, these SOIs are disclosed in "Report on patent application technology trends regarding the SOI (Silicon On Insulator) technology, Japanese Patent Office, [online], [Searched on May 8, 2011], the Internet <URL:http://www.jpo.go.jp/shiryou/pdf/gidou-houkoku/soi.pdf>", for example.

In addition, even if the thin film transistor 10 and the like of the radiation detector 20 are configured not to have light transparency (for example, even if the active layer 17 is formed of a material with no light transparency, such as amorphous silicon), the light-transmissive radiation detector 20 can be obtained by disposing the thin film transistor 10 and the like on the light-transmissive substrate 1 (for example, a flexible substrate formed of synthetic resin) and forming a portion of the thin film transistor 10, in which the thin film transistor 10 and the like are not formed, such that light is transmitted through the portion. Disposing the thin film transistor 10 and the like with no light transparency on the light-transmissive substrate 1 can be realized by the technique of separating a fine device block manufactured on a first substrate from the first substrate and disposing the fine device block on a second substrate, specifically, by applying an FSA (Fluidic Self-Assembly), for example. The FSA is disclosed in "Studies on technology of self-aligned arrangement of fine semiconductor blocks, University of Toyama, [online], [Searched on May 8, 2011], the Internet <URL:http://www3.u-toyama.ac.jp/maezawa/Research/FSA.html>", for example.

Figure 21:
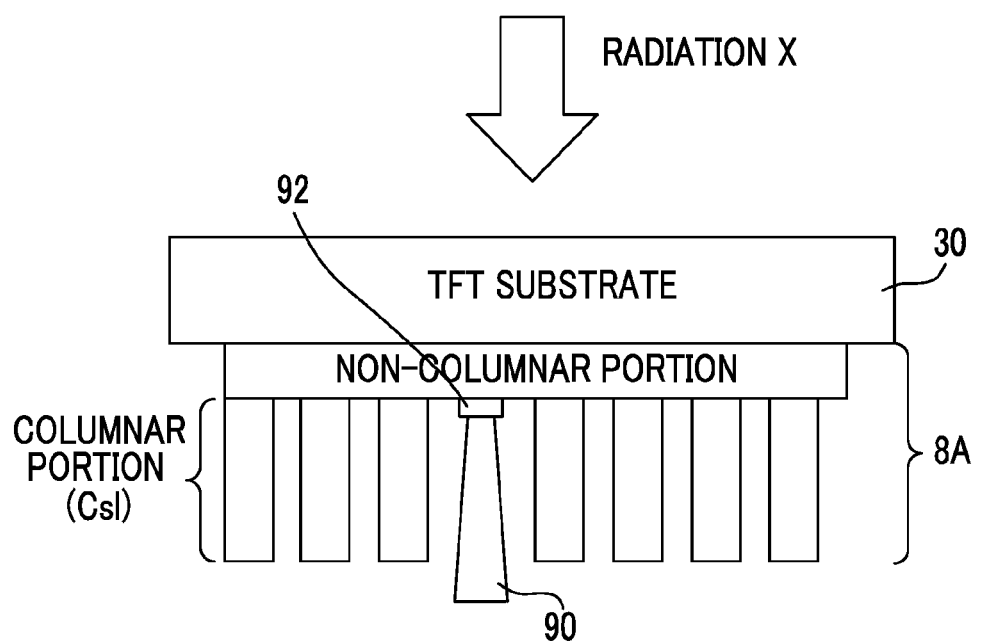
FIG. 21 is a cross-sectional view providing an explanation of an abnormal protrusion generated on columnar crystals.

Meanwhile, as described in the above embodiments, in a case where the scintillator is configured to include the columnar crystals such as CsI, as disclosed in JP2005-148060A as an example, in some cases, a protrusion portion 90 is formed by a partial abnormal growth of the columnar crystals as shown in FIG. 21 as an example, because of dust, splashing during the vapor deposition, unevenness of surface roughness of the TFT substrate, a defect of a pinhole or a protrusion of the TFT substrate, and the like. Herein, numerical reference 92 in the drawing denotes foreign matter caused by the protrusion portion 90 such as dust. As shown in FIGS. 9 and 15, when the radiation detector according to the above embodiments is configured by forming the scintillator 8A by direct vapor deposition on the TFT substrate, and when the radiation detector is used with ISS, the boundary side of the scintillator 8B becomes the protrusion portion 90 side.

As a solution when the protrusion portion 90 is formed as described above, as disclosed in JP2005-148060A, by applying a pressing force to the distal side of the columnar crystals, the protrusion portion 90 is crushed, the distal side is ground, or the protrusion portion 90 is melted so that the protrusion portion 90 can be removed.

Meanwhile, as a solution other than the one described above, a method of protecting the protrusion 90 by providing a buffering layer on the distal side of the scintillator 8A, without removing the protrusion portion 90 may be considered. Hereinafter, the detailed method will be described.

Figure 22:
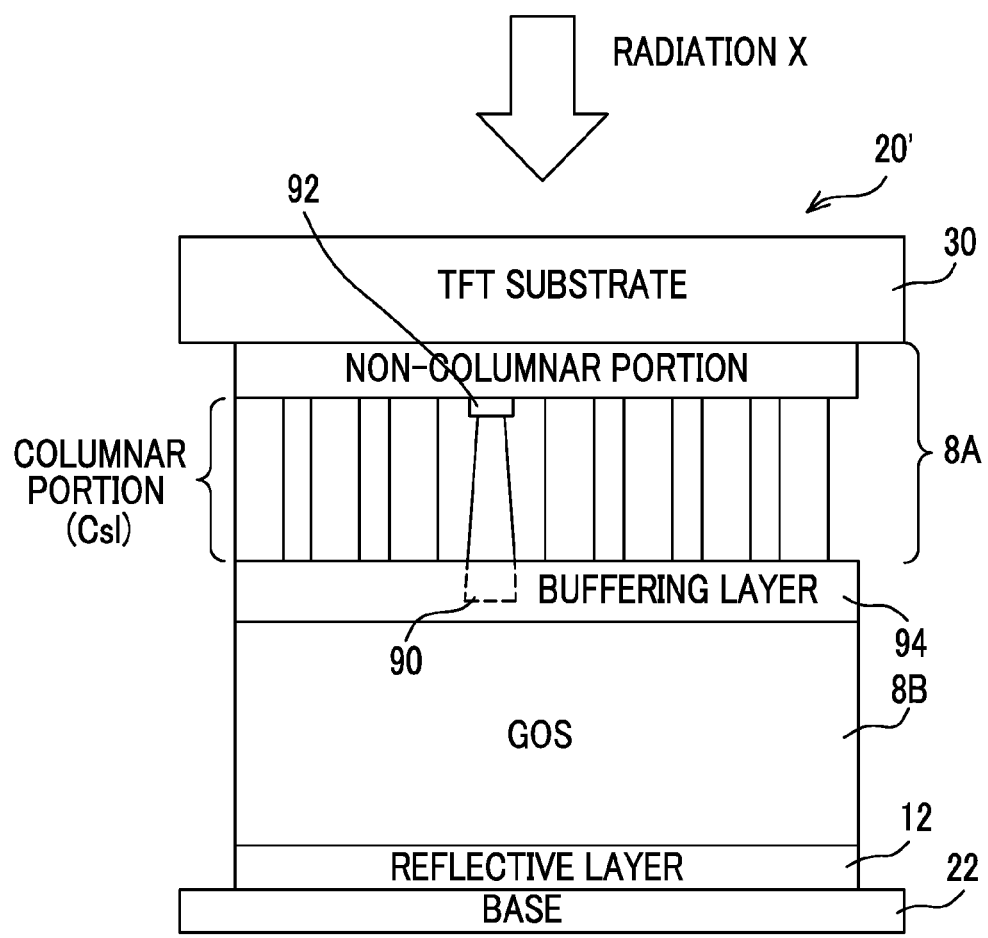
FIG. 22 is a cross-sectional view showing the configuration of a radiation detector according to another embodiment.

FIG. 22 shows a configuration example of a radiation detector 20' in a case of providing a buffering layer 94 which is transparent to visible light, with respect to the radiation detector 20 according to the first embodiment. As shown in the drawing, in the radiation detector 20', the buffering layer 94 is interposed between the distal side of the columnar crystals of the scintillator 8A and the scintillator 8B.

Figure 23:
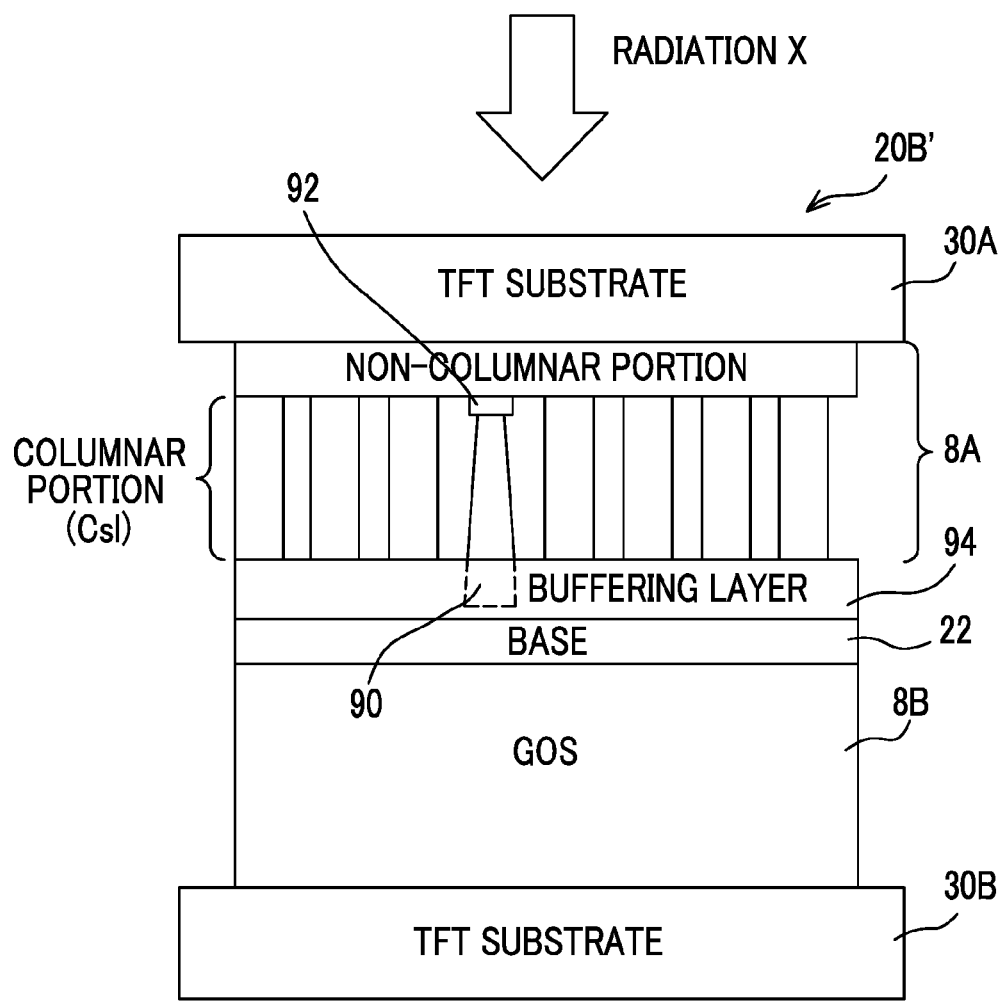
FIG. 23 is a cross-sectional view showing the configuration of a radiation detector according to another embodiment.

Meanwhile, FIG. 23 shows a configuration example of a radiation detector 20B' in a case of providing a buffering layer 94 with respect to the radiation detector 20B according to the second embodiment. As shown in the drawing, in the radiation detector 20B', the buffering layer 94 is interposed between the distal side of the columnar crystals of the scintillator 8A and the base 22.

Figure 24:
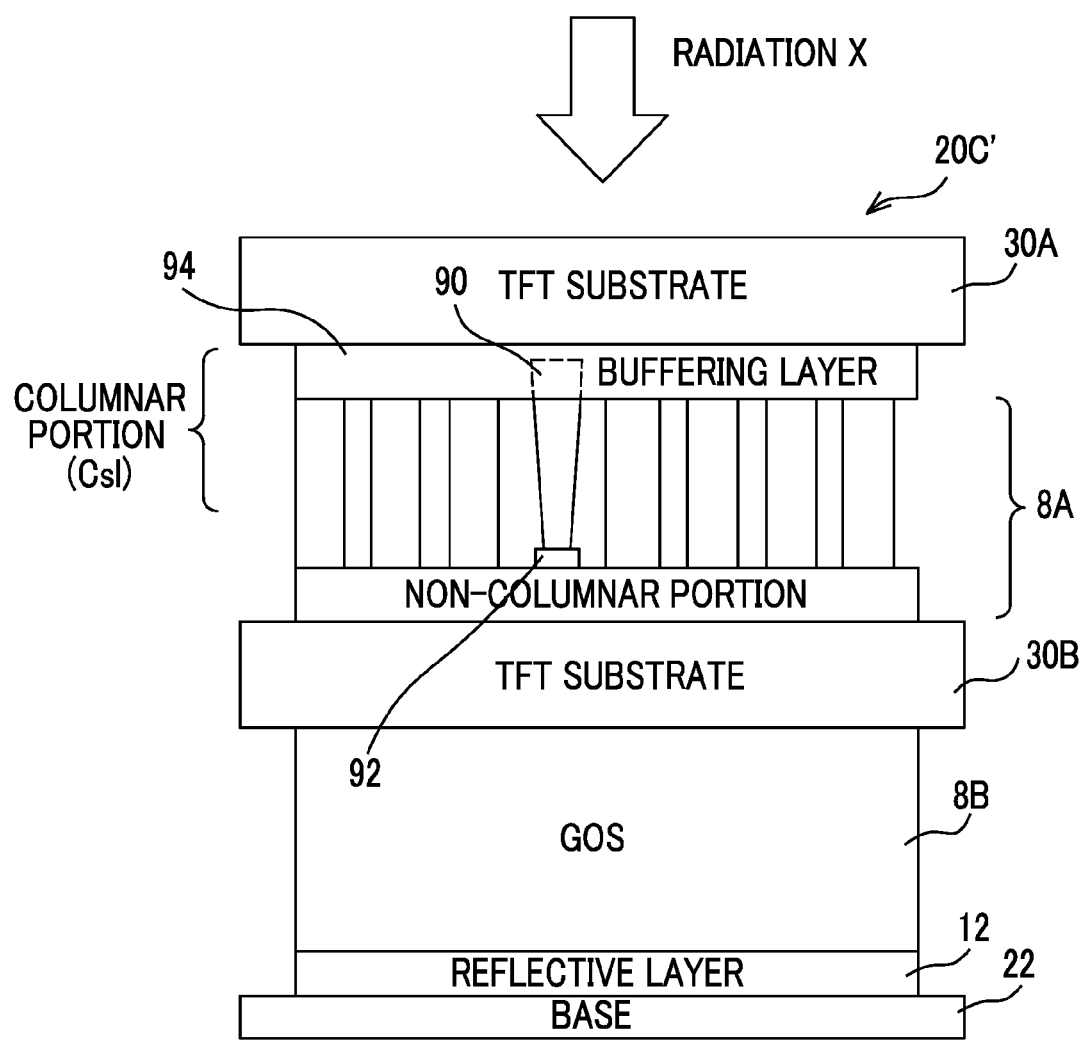
FIG. 24 is a cross-sectional view showing the configuration of a radiation detector according to another embodiment.

Further, FIG. 24 shows a configuration example of a radiation detector 20 C' in a case of providing a buffering layer 94 with respect to the radiation detector 20C shown in FIG. 16. As shown in the drawing, in the radiation detector 20C', the buffering layer 94 is interposed between the distal side of the columnar crystals of the scintillator 8A and the TFT substrate 30A.

Figure 25:
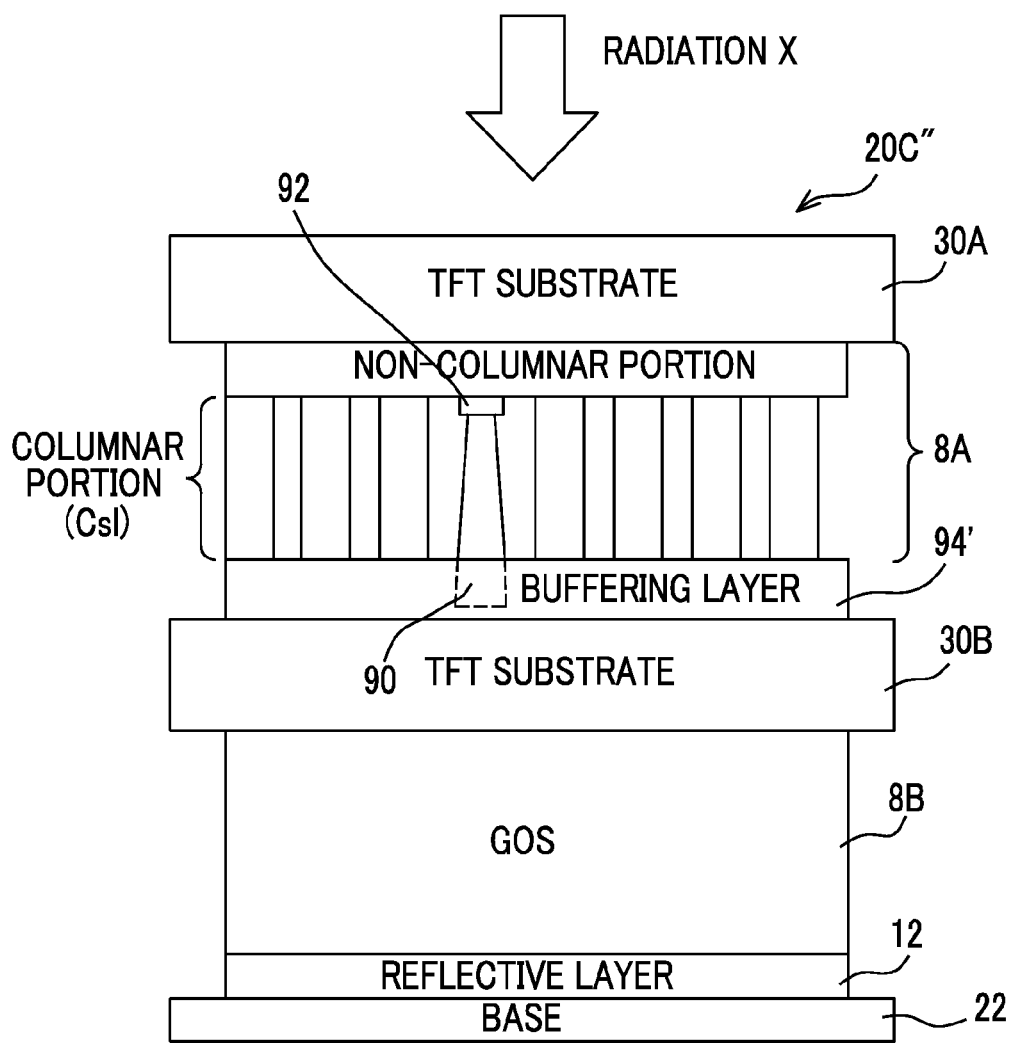
FIG. 25 is a cross-sectional view showing the configuration of a radiation detector according to another embodiment.

An example of FIG. 25 is a configuration example of a radiation detector 20C" in a case of providing a buffering layer 94 when the non-columnar portion side of the scintillator 8A is configured to be the TFT substrate 30A side with respect to the radiation detector 20C shown in FIG. 16. As shown in the drawing, in the radiation detector 20C", the buffering layer 94' is interposed between the distal side of the columnar crystals of the scintillator 8A and the TFT substrate 30B. In this case, it is not necessary for the buffering layer 94' to be transparent to visible light.

In any case of the radiation detectors 20', 20B', 20C', and 20C", as a joining method of the buffering layer 94 (94') and the members on both surfaces thereof, a bonding method with such as an adhesive, a method of pouch finishing (lamination) of the entire radiation detector, and the like can be applied. As a material of the buffering layer 94 (94'), for example, ultrathin silicon rubber (for example, thickness of 30 μm) such as "Silius" manufactured by Fuso Rubber Co., Ltd., silicon gel, urethane gel or the like can be appropriately used.

As described above, by protecting the protrusion portion 90 by the buffering layer, it is possible to prevent damage to the neighboring portion of the damage of the protrusion portion 90.

Figure 26:
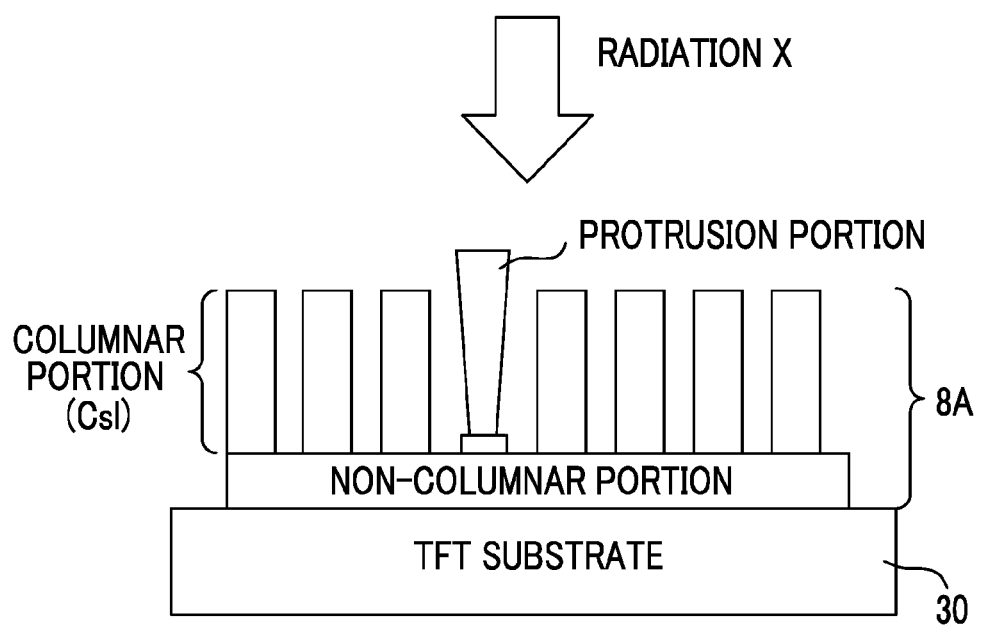
FIG. 26 is a cross-sectional view providing an explanation of problems with an abnormal protrusion generated on columnar crystals.

In the radiation detector used in a PSS in the related art, protecting the protrusion portion was not considered other than by removing the protrusion portion. As shown in FIG. 26 as an example, in the PPS in the related art, it is because that, since the protrusion portion is positioned always at the radiation incidence side, if the protrusion portion is not removed, the absorption states of the radiation of the protrusion portion and other normal portions greatly changes, and as a result, image defects are generated.

Meanwhile, in a case where the radiation detector according the embodiment is configured by forming the scintillator by the direct vapor deposition on the TFT substrate and in a case of using the radiation detector in ISS, since the protrusion portion is not positioned at the radiation incidence side, the change of radiation absorption states as described above is small so that it is not necessary to remove the protrusion portion.

As described in the embodiments, when the scintillator is configured to include the columnar crystals such as CsI, allowing the light generated in the scintillator to travel as much as possible in the columnar crystals of the scintillator makes it possible to obtain a radiological image with less blurring with the light guiding effect of the columnar crystals.

Figure 27:
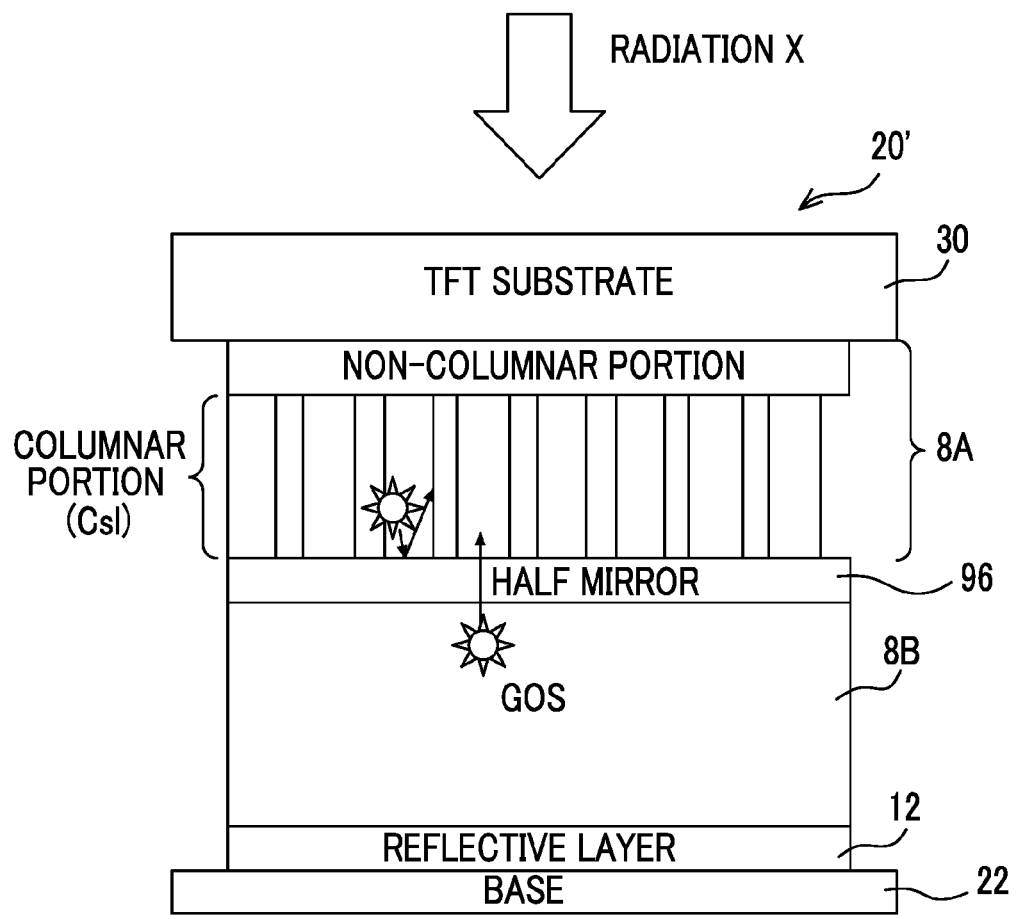
FIG. 27 is a cross-sectional view showing the configuration of a radiation detector according to another embodiment.
Figure 28:
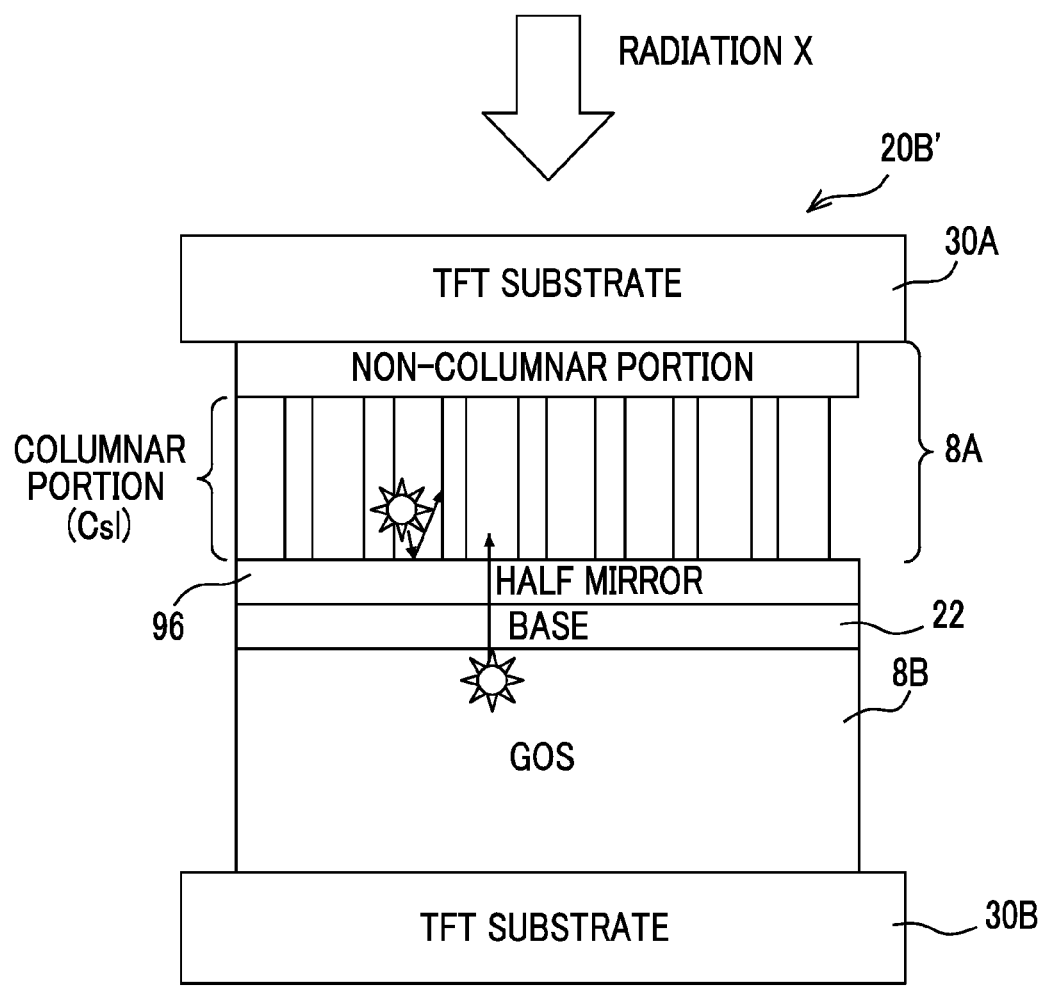
FIG. 28 is a cross-sectional view showing the configuration of a radiation detector according to another embodiment.

As shown in FIGS. 27 and 28 as an example, it is preferable that the radiation detector described in the embodiments reflect light from the scintillator 8A and the half mirror layer 96 which transmits light from the scintillator 8B be interposed between the scintillator 8A and the scintillator 8B. FIG. 27 is a configuration example of a case where the half mirror layer 96 is interposed with respect to the radiation detector 20 according to the first embodiment. FIG. 28 is a configuration example of a case where the half mirror layer 96 is interposed with respect to the radiation detector 20B according to the second embodiment.

In any case, a joining method of the half mirror layer 96 and the members on both surfaces thereof, a bonding method with such an adhesive, a method of pouch finishing (lamination) of the entire radiation detector, and the like can be applied.

As a material of the half mirror layer 96, for example, metals such as Ag, Al, NiAl or the like can be applied. A metal layer having a thickness of 2 nm or more and 100 nm or less can be applied. A method of preparing the half mirror layer 96 and the like is disclosed in "Industrial Research Institute of Niigata Prefecture, Technology and Research Report 2005 No. 34, "Study of New Functional Thin Films", [online], [Searched on Jul. 22, 2012], the Internet <URL: http://www.iri.pref.niigata.jp/pdf/houkoku/h16.pdf>", for example. Accordingly, explanation thereof will be omitted.

What is claimed is:

1. A radiation detector comprising:
   a substrate having a first photoelectric conversion element, which has one surface from which a radiation is emitted and the other surface from which light is emitted and which generates electric charges corresponding to the light, and a first switching element for reading the electric charges generated by the first photoelectric conversion element;
   a first phosphor layer which is laminated on the other surface of the substrate, generates first light corresponding to a radiation emitted through the substrate, and is configured to include columnar crystals;
   a second phosphor layer which is laminated on a surface of the first phosphor layer not facing the substrate, generates second light corresponding to a radiation emitted through the first phosphor layer, and has different energy characteristics of absorbed radiations from the first phosphor layer; and
   a second substrate which is provided on an opposite surface of the second phosphor layer to a surface laminated on the first phosphor layer and which has a second photoelectric conversion element, which generates electric charges corresponding to the second light generated by the second phosphor layer, and a second switching element for reading the electric charges generated by the second photoelectric conversion element,
   wherein light emitted from the other surface is at least one of the first light and the second light; and
   wherein distal ends of the columnar crystals are position at the second phosphor layer side.

2. The radiation detector according to claim 1, wherein the first phosphor layer has non-columnar crystals formed on a surface laminated on the substrate.

3. The radiation detector according to claim 2, wherein the non-columnar crystals provide a layer having porosity.

4. The radiation detector according to claim 3, wherein the non-columnar crystals have a granular shape.

5. The radiation detector according to claim 1, wherein a reflective layer is laminated on an opposite surface of the second phosphor layer to a surface laminated on the first phosphor layer.

6. The radiation detector according to claim 1, wherein, in the first phosphor layer, distal ends of the columnar crystals are formed to be flat.

7. The radiation detector according to claim 1, wherein, in the first phosphor layer, distal ends of the columnar crystals are formed to be flat.

8. The radiation detector according to claim 1, wherein the second phosphor layer is configured to include a material with a larger atomic number than an atomic number of an element which forms the columnar crystals.

9. The radiation detector according to claim 1, wherein the first phosphor layer is configured to include columnar crystals of CsI, and the second phosphor layer is configured to include GOS.

10. The radiation detector according to claim 1, further comprising:
    a buffering layer which is interposed between distal ends of columnar crystals and an object to be laminated on the distal ends, is directly laminated at least on the distal ends, and is transparent to visible light.

11. The radiation detector according to claim 10, wherein the buffering layer is composed of a material having elasticity and protects a protrusion of columnar crystals.

12. The radiation detector according to claim 11, wherein the buffering layer is composed of a material including at least one of silicon rubber, silicon gel, and urethane gel.

13. The radiation detector according to claim 10, wherein a thickness of the buffering layer in a laminating direction of the columnar crystals is larger than that of the protrusion of the columnar crystals.

14. The radiation detector according to claim 1, further comprising:
    a half mirror layer which is interposed between the first phosphor layer and the second phosphor layer, reflects light from the first phosphor layer, and allows the light to be transmitted from the second phosphor layer.

15. A radiological image radiographing apparatus comprising:
    the radiation detector according to claim 1; and
    a generation unit for generating image information indicated by electric charges read from the radiation detector.

16. A radiological image radiographing apparatus comprising:
   the radiation detector according to claim 1; and
   a generation unit for generating new image information by adding, for each corresponding pixel, the image information indicated by electric charges read from the substrate and the second substrate provided in the radiation detector.

17. A radiation detector comprising:
   a substrate having a first photoelectric conversion element, which has one surface from which a radiation is emitted and the other surface from which light is emitted and which generates electric charges corresponding to the light, and a first switching element for reading the electric charges generated by the first photoelectric conversion element;
   a first phosphor layer which is laminated on the other surface of the substrate, generates first light corresponding to a radiation emitted through the substrate, and is configured to include columnar crystals;
   a second phosphor layer which is laminated on a surface of the first phosphor layer not facing the substrate, generates second light corresponding to a radiation emitted through the first phosphor layer, and has different energy characteristics of absorbed radiations from the first phosphor layer; and
   a second substrate which is provided between the first phosphor layer and the second phosphor layer and which has a second photoelectric conversion element, which generates electric charges corresponding to the second light generated by the second phosphor layer, and a second switching element for reading the electric charges generated by the second photoelectric conversion element;
   wherein light emitted from the other surface is at least one of the first light and the second light.

18. The radiation detector according to claim 17,
   wherein a side of the first phosphor layer laminated on the substrate is distal ends of the columnar crystals.

19. The radiation detector according to claim 17,
   wherein a reflective layer is laminated on an opposite surface of the second phosphor layer to a surface laminated on the second substrate.

20. The radiation detector according to claim 17,
   wherein the photoelectric conversion element of the second substrate is configured to include an organic photoelectric conversion material.

21. The radiation detector according to claim 17,
   wherein at least one of the substrate and the second substrate is a flexible substrate.

22. The radiation detector according to claim 17,
   wherein, in the first phosphor layer, distal ends of the columnar crystals are formed to be flat.

23. The radiation detector according to claim 17,
   wherein the second phosphor layer is configured to include a material with a larger atomic number than an atomic number of an element which forms the columnar crystals.

24. The radiation detector according to claim 17,
   wherein the first phosphor layer is configured to include columnar crystals of CsI, and the second phosphor layer is configured to include GOS.

25. The radiation detector according to claim 17, further comprising:
   a buffering layer which is interposed between distal ends of columnar crystals and an object to be laminated on the distal ends, is directly laminated at least on the distal ends, and is transparent to visible light.

26. The radiation detector according to claim 17, further comprising:
   a half mirror layer which is interposed between the first phosphor layer and the second phosphor layer, reflects light from the first phosphor layer, and allows the light to be transmitted from the second phosphor layer.

27. A radiological image radiographing apparatus comprising:
   the radiation detector according to claim 17; and
   a generation unit for generating image information indicated by electric charges read from the radiation detector.

28. A radiological image radiographing apparatus comprising:
   the radiation detector according to claim 17; and
   a generation unit for generating new image information by adding, for each corresponding pixel, the image information indicated by electric charges read from the substrate and the second substrate provided in the radiation detector.

* * * * *